(12) United States Patent
Zamora et al.

(10) Patent No.: US 7,795,314 B2
(45) Date of Patent: Sep. 14, 2010

(54) PROTECTIVE ROLE OF SEMAPIMOD IN NECROTIZING ENTEROCOLITIS

(75) Inventors: Ruben Zamora, Pittsburgh, PA (US); Henri R. Ford, La Canada, CA (US); Thais Sielecki-Dzurdz, Kennett Square, PA (US); Vidal F. De La Cruz, Phoenixville, PA (US)

(73) Assignee: Cytokine PharmaSciences, Inc., King of Prussia, PA (US)

( * ) Notice: Subject to any disclaimer, the term of this patent is extended or adjusted under 35 U.S.C. 154(b) by 376 days.

(21) Appl. No.: 11/421,666

(22) Filed: Jun. 1, 2006

(65) Prior Publication Data

US 2007/0282005 A1 Dec. 6, 2007

Related U.S. Application Data

(60) Provisional application No. 60/685,875, filed on Jun. 1, 2005.

(51) Int. Cl.
 *A61K 31/165* (2006.01)
(52) U.S. Cl. ................................... 514/615
(58) Field of Classification Search ............. None
 See application file for complete search history.

(56) References Cited

U.S. PATENT DOCUMENTS

2006/0211752 A1* 9/2006 Kohn et al. ............ 514/389

FOREIGN PATENT DOCUMENTS

WO  02/00613 A2  1/2002
WO  WO2004/004763  1/2004

OTHER PUBLICATIONS

The Merck Manual, 17th edition (1999), pp. 2195-2196.*
Waetzig et al., Aliment. Pharmacol. Ther., 18:17-32 (2003).*
Haichao Wang, et al., "Suppression of High Mobility Group-1 Protein (HMG-1) Release by a Macrophage-deactivating Agent CNI-1493", Acad. Emerg. Med. 8(5): 513. 2001.
Ryo Takeda, et al., "Blockade of Endogenous Cytokines Mitigates Neointimal Formation in Obese Zucker Rats", Circulation 1398-1406, Mar. 22, 2005.
Guoqi Zhang, et al., "Borna Disease Virus Phosphoprotein Represses p53-Mediated Transcriptional Activity by Interference with HMGB1", Journal of Virology, vol. 77, No. 22, 12243-12251, Nov. 2003.
Susanne Mueller, et al., "The double life of HMGB1 chromatin protein: architectural factor and extracellular signal", The EMBO Journal, vol. 20, No. 16, pp. 4337-4340, 2001.
Andrew E. Sama, et al., "Bench to Bedside: HMGB1—A Novel Proinflammatory Cytokine and Potential Therapeutic Target for Septic Patients in the Emergency Department", Acad. Emerg. Med. vol. 11, No. 8, 867-873, Aug. 2004.
Wolfgang Doppler, et al., "Expression Level-Dependent Contribution of Glucocorticoid Receptor Domains for Functional Interaction with STAT5", Molecular and Cellular Biology, vol. 21, No. 9, p. 3266-3279, May 2001.
Qing He, et al., "Steroid hormones induce HMG1 overexpression and sensitize breast cancer cells to cisplatin and carboplatin", Proc. Nat. Acad. Sci. vol. 97, No. 11, p. 5768-5772, May 23, 2000.
Guglielmo Sorci, et al., "Amphoterin Stimulates Myogenesis and Counteracts the Antimyogenic Factors Basic Fibroblast Growth Factor and S100B via RAGE Binding", Molecular and Cellular Biology, vol. 24, No. 11, p. 4880-4894, Jun. 2004.
Ina Poser, et al., "Upregulation of HGM1 Leads to Melanoma Inhibitory Activity Expression in Malignant Melanoma Cells and Contributes to Their Malignancy Phenotype". Molecular and Cellular Biology, vol. 23, No. 8, p. 2991-2998, Apr. 2003.
Taichiro Goto, et al., Abstract—"Importance of tumor necrosis factor-alpha cleavage process in post-transplantation lung injury in rats", American Journal of Respiratory and Critical Care Medicine, vol. 170, No. 11, pp. 1239-1246, Dec. 1, 2004.
Stefania Guazzi, et al., Abstract—"HMGB1, an architectural chromatin protein and extracellular signalling factor, has a spatially and temporally restricted expression pattern in mouse brain", Gene Expression Patterns, vol. 3, No. 1, pp. 29-33, Mar. 2003.
J.M. Wyss, et al., Abstract—"beta-Neuregulin induces genes related to neuronal differentiation and outgrowth in rat hippocampal neurons in vitro", Society for Neuroscience Abstracts, vol. 27, No. 1, p. 1242, 2001.
Odette Prat, et al., Abstract—"Transcriptomic and proteomic responses of human renal HEK293 cells to uranium toxicity", Proteomics, vol. 5, No. 1, pp. 297-306, Jan. 2005.
Hiroki Kuniyasu, et al., Abstract—"Differential effects between amphoterin and advanced glycation end products on colon cancer cells," Int J Cancer, vol. 104, No. 6, pp. 722-727, May 10, 2003.

* cited by examiner

*Primary Examiner*—Phyllis G. Spivack
(74) *Attorney, Agent, or Firm*—John K. Pike; Law Office of John K. Pike, PLLC

(57) ABSTRACT

A method is described wherein semapimod is administered, or a salt thereof, or a combination of semapimod and a salt thereof, for the treatment of necrotizing enterocolitis.

9 Claims, 12 Drawing Sheets

PROTECTIVE ROLE OF SEMAPIMOD IN NECROTIZING ENTEROCOLITIS

CROSS REFERENCE TO RELATED APPLICATIONS

This application is based on, and claims priority to, U.S. Provisional Application Ser. No. 60/685,875, filed Jun. 1, 2005, the entire contents of which are hereby incorporated by reference.

This work was supported in part by the RO1-AI-14032 grant from the National Institites of Health (Bethesda, MD). The government may have rights in this invention.

BACKGROUND

Field

The present invention relates to guanyhydrazone-moiety-containing compounds and their use in the prevention, treatment, and inhibition of conditions, such as inflammatory conditions.

DESCRIPTION OF THE SEVERAL EMBODIMENTS

Figure 1:
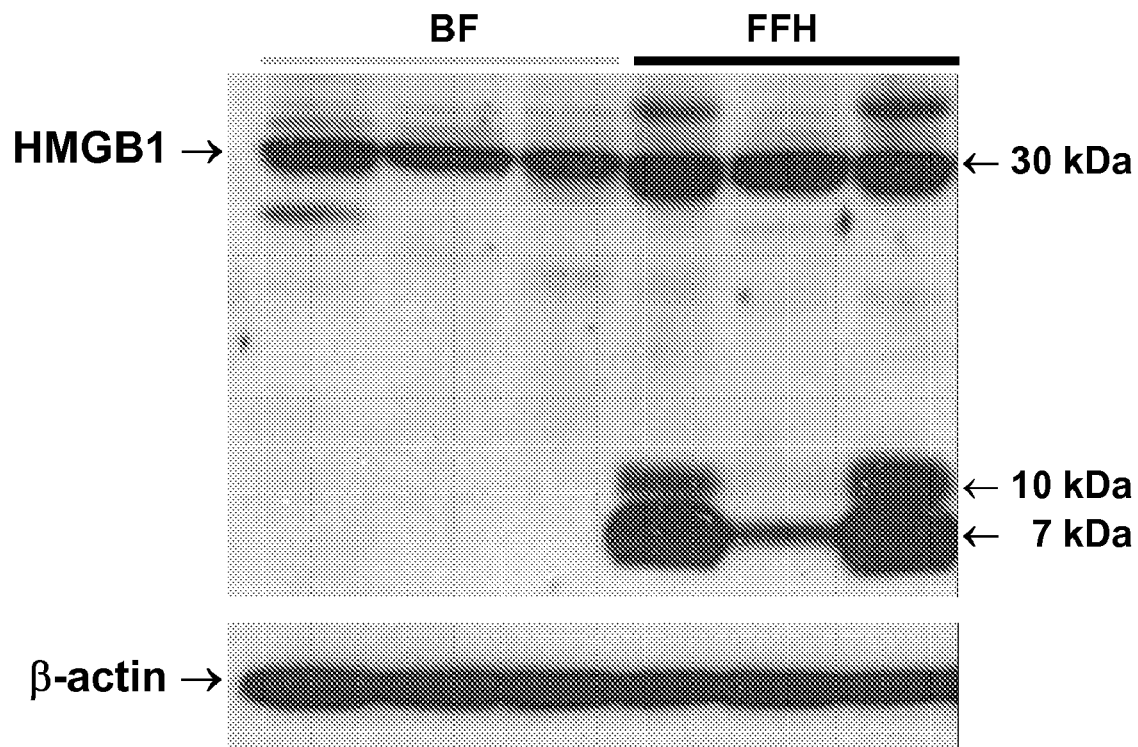
FIG. 1 shows the HMGB1 is elevated in formula-fed animals exposed to hypoxia.
Figure 1:
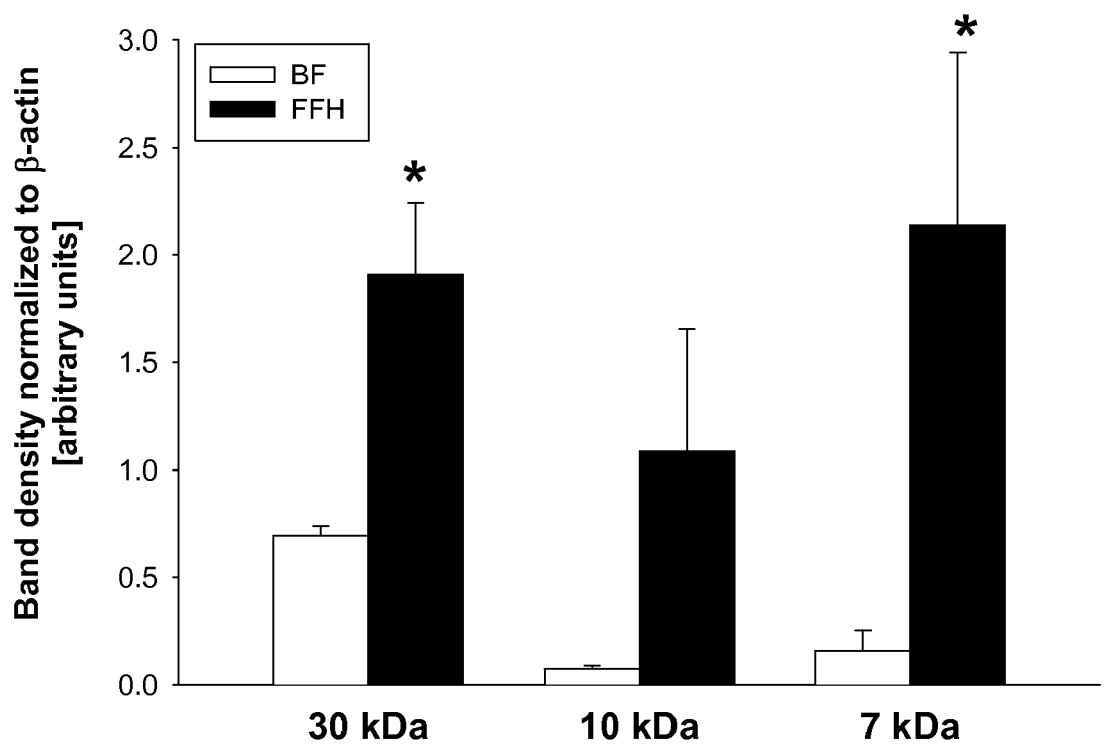

Necrotizing enterocolitis (NEC) is the most frequent and the most lethal disease that affects the gastrointestinal tract of the premature infant (16). The overall mortality rate for patients with NEC ranges from 10 to 70% (22) and approaches 100% for patients with the most severe form of the disease, which is characterized by involvement of the entire bowel (pannecrosis) (37). Survivors may develop short-bowel syndrome, recurrent bouts of central line associated sepsis, malabsorption and malnutrition, liver failure as a result of longstanding administration of total parenteral nutrition, and eventually may require liver-small bowel transplantation (27; 37). Thus, NEC represents one of the most important diseases seen in the neonatal population.

Several risk factors for NEC have been identified, including low birth weight, formula feeding, bacterial colonization of the gut, and hypoxia (1-3). Several experimental animal models have been reported (4; 10; 12; 14; 20) which have intestinal hypoxia as the common denominator. Other risk factors including prematurity (47), hypoxin (26), formula feeding (18), bacterial infection (40), and intestinal ischemia (1) have been implicated in the pathogenesis of NEC. In order to understand the pathogenesis of NEC, others have relied on intravenous administration of pro-inflammatory cytokines or invasive surgical procedures, such as occlusion of the mesenteric vessels, to reproduce the morphological and clinical changes seen in infants with NEC (16). However, these artificial insults do not parallel the human disease. To understand the pathogenesis of this disease, the present inventors have developed a consistent and reproducible rat model that relies on formula feeding and hypoxia, two major risk factors for NEC (32).

The present inventors modified an experimental model (32) so that newborn rats were fed with formula twice a day and exposed to hypoxia for a longer period of time (10 min. instead of 3 min.). Examining a larger number of animals the present inventors observed a higher mortality rate in the FFH animals as compared to the BF group. As used herein, BF represents breast-fed animals left with their mothers (controls), and FFH are formula-fed pups exposed to hypoxia. Although malnutrition could be a contributing factor (the volume of formula consumed by the neonatal rats is less than the volume of milk consumed by breast-fed pups), there was no apparent cause of death for most of the animals in the FFH group. The significant difference in mortality could only be attributed to aspiration during gavage. The longer exposure to hypoxia, however, exacerbated the inflammatory changes seen in the intestine of the FFH group and rendered the neonatal rats more susceptible to gut barrier failure as shown by the increased incidence of NEC starting at day 3 after birth.

The present inventors have shown that NEC is characterized by the presence of a number of pro-inflammatory cytokines, both in experimental and in human NEC (32; 33). There, the present inventors have examined the expression of the protein called high mobility group box 1 (HMGB1) in the small intestine of newborn rats with NEC. Wang et al. have identified and characterized the high mobility group box-1 protein (HMGB1, previously known as HMG1 or amphoterin) as a potential late mediator of lethality in a mouse model (44) and a regulator of human monocyte proinflammatory cytokine synthesis (3). This protein belongs to the HMGB group, one of the three superfamilies of the HMG nuclear proteins subdivided according to their characteristic functional sequence motifs. The functional motif of this family is called the HMG-box and according to the revised nomenclature of the HMG nuclear proteins, the HMG-1 has been renamed to HMGB1 (9). HMGB1 is 30 kDa nuclear and cytosolic protein member of the high-mobility group protein superfamily that has been widely studied as a transcription as well as growth factor, HMGB1 is also defined as a cytokine because it stimulates proinflammatory responses in monocytes/macrophages, is produced during systemic and local inflammatory responses, has been identified as a late mediator of lethal systemic inflammation (e.g. endotoxaemia and sepsis), and is required for the full expression of inflammation in animal models of endotoxemia, sepsis and arthritis (2; 45). Until the present invention, however, the expression of HMGB1 in the injured intestine and its role in intestinal inflammation and in particular in NEC, was not known. HMGB1 is produced by nearly all cell types, but cellular levels vary with development and age (45). As expected, the present inventors found a high expression of HMGB1 in the ileum of BF newborn rats. However, maximal expression of HMGB1 in the ileal mucosal scrapings of FFH newborn rats at day 4 coincided with the marked appearance of morphological characteristics of NEC. Those animals that showed moderate to severe intestinal damage as assessed by histology also showed an increased expression of a lower molecular weight (e.g., below 30 kDa) protein detected with the same anti-HMGB1 polyclonal antibody (as a 7-10 kDa band).

Numerous inflammatory mediators have been implicated in the cascade leading to the hemodynamic instability associated with sepsis. Elevated levels of IL-6 and TNF-α have been measured in infants with NEC, bacterial sepsis, or meningitis (21). The present inventors have shown that nitric oxide (NO) modulates intestinal changes in septic shock (17; 43). Furthermore, the end products of NO metabolism have been shown to be elevated in newborn infants as well as in adult patients clinical sepsis (34; 41). Several studies suggest these and other mediators of sepsis are also involved in the pathogenesis of NEC. In this context, the present inventors have previously reported the upregulation of iNOS mRNA in the intestine of infants with acute NEC, and its downregulation by the time of intestinal stoma closure, after the infants have recovered from the acute inflammatory process (17). A similar pattern was seen for IFN-γ, but not for IL-1, IL-6, TGF-beta, or TNF-α. The pattern of cytokine mRNA expression in our model of experimental NEC parallels that seen in patients with NEC (17).

It has been shown that HMGB1$^{-/-}$ necrotic cells have a greatly reduced ability to promote inflammation, which proves that the release of HMGB1 can signal the demise of a cell to its neighbors (39). Apoptotic cells, however, do not release HMGB1 even after undergoing secondary necrosis and partial autolysis, and thus fail to promote inflammation even if not cleared promptly by phagocytic cells (39). HMGB1 is either actively secreted by monocytes/macrophages or passively released from necrotic cells from any tissue (45). Since in experimental NEC enhanced epithelial apoptosis is an initial event underlying the gross tissue necrosis of the intestinal wall (11; 25), it is believed that the elevated levels of HGMB1 found in the ileal mucosal scrapings of FFH newborn rats suggest that there is more synthesis of HMGB1 protein and/or more translation from the nucleus to the cytoplasm of the protein ready to get released into the extracellular milieu, where it mediates downstream inflammatory responses. Such HMGB1-related responses have been reported in endotoxemia, arthritis and sepsis (2). Like their finding with rat NEC, the present inventors found that the intestinal segments of infants with acute NEC showed greater expression of HMGB1 than the intestinal segments from non-NEC patients. Thus, without wishing to be bound by theory, it is believed that an overexpression of HMGB1 may be related to the intestinal damage induced by hypoxia and formula feeding in experimental NEC as well as in human NEC.

Little is known about how the HMGB1 mRNA is transcriptionally regulated. The present inventors previously found that among the several DNA repair genes that were affected by iNOS in murine hepatocytes, there was an increased expression of the gene coding for the high mobility group protein HMG-2 as determined by microarray DNA analysis (49). However, the exact relationship and whether iNOS-derived NO alters the expression or activity of HMG proteins and specifically of HMGB1 remain to be investigated. Although HMGB1 has not been associated with gene transcription in vivo, it can stimulate transcription in vivo (45). Thus, it is also possible that elevated levels of HMGB1 affect the expression of other cell-death related genes in the experimental model of NEC.

The present inventors have found that the cell death related protein HMGB1 is differentially expressed in the injured small intestine of newborn rats in experimental NEC and in the inflamed intestine of human infants with acute NEC. The present inventors evaluated the effects of the macrophage deactivator semapimod (formerly known as CNI-1493) on the expression of pro-apoptotic and pro-inflammatory proteins and on the severity of intestinal inflammation in their experimental model of NEC, as well as its effects on rat intestinal epithelial cells challenged with bacterial LPS. Semapimod (formerly known as CNI-1493), is a tetravalent guanylhydrazone known to inhibit mouse macrophage arginine transport and NO production and to suppress the release of proinflammatory cytokines (7). The present inventors show that this macrophage-deactivating drug inhibits the expression and accumulation of HMGB1 in the ileal mucosal scrapings of FFH animals thereby limiting the degree of intestinal injury caused by formula feeding and exposure to hypoxia. The fact that semapimod did not completely prevent the occurrence of NEC-like morphological changes in the experimental model merely confirms the complexity of this disease and implies that other mechanism(s) are also involved in its pathogenesis. It is clear, however, that HMGB1 is an important mediator of hypexia-induced gut injury and that suppression of pro-inflammatory cytokines with inhibitors such as semapimod partially protects against intestinal epithelial cell death both in vitro and in vivo.

Accordingly, one embodiment is the use and/or administration of semapimod and other guanylhydrazone containing compounds for the inhibition, treatment, and/or prevention of NEC to a subject in need thereof.

Another embodiment is the use and/or administration of semapimod and other guanylhydrazone containing compounds for the inhibition, treatment, and/or prevention of NEC to a human subject in need thereof. In one embodiment, the subject is a human infant, for example one with one or more of low-birth weight, formula feeding, bacterial colonization of the gut, hypoxia, and/or other conditions associated with the release of HMGB1.

Outside the cell HMGB1 binds with high affinity to the receptor for advance glycation end-products (RAGE), a transmembrane receptor of the immunoglobulin superfamily which is in part responsible for the receptor signal transduction of HMGB1 (24; 44). RAGE is expressed on monocytes/macrophages, endothelial cells, neurons and smooth-muscle cells (2). The accumulation of RAGE ligands leads to inflammatory disorders and the biology of RAGE is driven by the settings in which these ligands accumulate, such as diabetes, inflammation, neurodegenerative disorders and tumors (8). Although one study has shown that a human colon adenocarcinoma cell line expresses RAGE (51), until the present invention, the expression of this protein in nontransformed intestinal epithelial cells or normal intestinal tissue has not been reported. In their rat model, the present inventors could hardly detect any RAGE in the ileal mucosal scrapings of BF newborn rats. However, there was a higher expression of RAGE in the intestinal samples from FFH animals analyzed using an anti-RAGE antibody that detects two bands in the 45 kDA range (the RAGE protein pre and post-glycosylation in mouse lung extract) and a 25 kDa protein believed to be a proteolytic degradation product. The intensity of the 25 kDa band was significantly higher than the 45 kDa band in the FFH animals. Without wishing to be bound by theory, it is believed that this finding is not due to total protein degradation as shown by the normal β-actin levels. The present inventors have found that not only the expression of HMGB1 was significantly reduced by semapimod but also that of its receptor RAGE. Accordingly, it is believed that upregulation of RAGE is involved in the intestinal injury caused by formula feeding and hypoxia. In this respect, a recent study using novel animal models with defective or tissue-specific RAGE expression showed that deletion of RAGE provides protection from the lethal effects of septic shock caused by cecal ligation and puncture (29). It should be noted, however, that although RAGE has been shown to interact with HMGB1, other putative HMGB1 receptors are known to exist but have not been characterized yet. A recent study showed that while RAGE played only a minor role in macrophage activation by HMGB1, the interactions of HMGB1 with TLR 2 and TLR 4 could explain the ability of HMGB1 to generate inflammatory responses that are similar to those initiated by LPS (35). Accordingly, another embodiment relates to the role of RAGE and other receptors in mediating inflammatory responses to HMGB1, and it is believed that RAGE accumulation and degradation accompanies the upregulation of its ligands HMGB1 associated with formula feeding and hypoxia-induced intestinal injury in experimental NEC. As such, another embodiment is the inhibition and/or downregulation of the HMGB1 receptor, RAGE, by the administration with semapimod and/or guanylhydrazone containing compounds.

As in many other cell types and tissues, intestinal apoptosis and cell death are the result of different pathways that involve a number of pro-inflammatory cytokines and mediators other than HMGB1. The present inventors found that expression of Bax and Bad, two pro-apoptotic members of the Bcl-2 family of proteins, were significantly uupregulated by formula feeding and hypoxia in the mucosal scrapings of FFH animals as compared to BF controls. Expression of both proteins in FFH pups was also significantly decreased when the animals where administered the drug semapimod. Similarly, other proteins like iNOS and COX-2 whose altered expression has been associated with inflammation in a number of experimental and clinical conditions (see 28; 46; 50) for reviews), were elevated in the terminal ileum of FFH newborn rats compared to BF controls and downregulated when the animals were administered the drug semapimod. Although the present inventors did not assess the integrity of the mucosal barrier, it has previously been shown that HMGB1 is capable of causing derangements in intestinal barrier function in cultured Caco-2 human enterocytic monolayers and that this effect depends on the formulation of NO and peroxynitrite (38). Thus, without wishing to be bound by theory, it is believed that the protection conferred by semapimod also be related to its ability to inhibit the formula feeding plus hypoxia-induced increase in the intestinal permeability by decreasing both HMBG1 and iNOS protein expression.

Accordingly, another embodiment relates to the administration of semapimod and/or guanylhydrazone containing compounds to decrease one or both of HMGB1 and iNOS protein expression.

Since bacterial colonization is an important factor in the pathogensis of NEC, it is necessary to understand the response of intestinal epithelial cells to LPS. In the model described herein, this becomes even more important because the animals are not kept in a pathogen free environment. The present inventors have found that LPS activates the mitogen-activated protein kinase (MAP kinase) p38 both in IEC-6 rat intestinal epithelial cells and in ileal mucosal scrapings cultured ex vivo (19). This increase in p38 activation could significantly be inhibited upon pre-incubation of IEC-6 cells with semapimod in a concentration-dependent fashion. More importantly, the inhibitory effect of semapimod rather than a non-specific inhibitory effect seems to be a selective effect on the LPS significantly pathway. That is illustrated by the fact that semapimod inhibited p38 activation only in LPS treated cells but not in cells exposed to ONOO$^-$, the toxic NO-related species that also activates p38. Without wishing to be bound by theory, it is believed that diverse effects of semapimod are tissue specific and confer protection against the hemodynamic and inflammatory responses to LPS (31). Also, semapimod has previously been shown to inhibit the expression of the pro-inflammatory cytokines through a pathway involving the MAP kinases, specifically to inhibit the phosphorylation and activation of p38 MAP kinase in both human monocytes and the murine macrophage cell line RAW 264.7 (13; 30). Inflammatory MAP kinases, in particular p38 and JNK, are critically involved in the pathogenesis of Crohn's disease (23), and their involvement in the regulation of inflammatory responses in the gut is within the scope of the present invention.

A neural pathway, termed the "cholinergic anti-inflammatory pathway", involves vagus nerve stimulation that inhibits the release of TNF, HMGB1, and other cytokines, and protects against endotoxemia and ischemia-reperfusion injury (6). Examining the effects of pharmacological and electrical stimulation of the intact vagus nerve in adult male Lewis rats subjected to endotoxin-induced shock, it was found that intact vagus nerve signaling was required for the anti-inflammatory action of semapimod (6). In that study, intracerebroventricular (icv.) administration of semapimod was 100,000-fold more effective in suppressing endotoxin-induced TNF release and shock as compared with intravenous rate. Although icv. administration of the drug is extremely difficult due to the small size and sensitivity of newborn pups, such a finding would not preclude this administration route to human subjects, such as neonates. Without wishing to be bound by theory, one possible mechanism through which semapimod may be protective is the "cholinergic anti-inflammatory pathway" in the development of both experimental and human NEC.

In summary, the present invention have found that the pro-inflammatory protein HMGB1 and its receptor RAGE are elevated in the ileal mucosa of formula-fed newborn rats exposed to hypoxia. The present invention show that the synthetic guanylhydrazone semapimod, a cytokine inhibitor and MAP kinase blocker, inhibits the upregulation of both HMBG1 and RAGE as well as of other proinflammatory mediators, thereby limiting the intestinal injury caused by formula feeding and hypoxia in experimental NEC. In addition, the present inventors have found that semapimod selectively affects the activation of p38 MAP kinase by LPS in IEC-6 intestinal epithelial cells supporting the involvement of the MAP kinases in the protective effect of semapimod against bacterial LPS-induced intestinal injury. The present inventors have identified HMGB1 and RAGE as important mediators of enterocyte apopotosis/cell death hypoxia-induced gut barrier failure associated with NEC. Semapimod is currently being developed as a potential treatment of Crohn's disease and other inflammatory pathologies (42). The present inventors have found a method to suppress the release of pro-inflammatory cytokines and inhibit the expression and activity of cytotoxic molecules such as HMGB1 with inhibitors like semapimod, and the present compounds are also useful in a therapeutic modality to combat inflammatory conditions such as NEC. Other guanylhydrazone-containing compounds described herein are expected to have the same effect.

Suitable compounds include guanylhydrazone-containing compounds described herein, such as a semapimod. The guanylhydrazone-containing compound may be used in pharmaceutical, medicinal, veterinary, agricultural, and analytical applications and/or for other commercial purposes in accordance with the present methods.

Accordingly, one embodiment is the use and/or administration of semapimod and other guanylhydrazone-containing compounds for the inhibition, treatment, and/or prevention of NEC to a subject in need thereof.

Another embodiment is the use and/or administration of semapimod and other guanylhydrazone-containing compounds for the inhibition, treatment, and/or prevention of any of NEC, a condition associated with the release of HMGB1, a condition associated with the release of iNOS protein, or a condition associated with the release of RAGE, or a combination thereof to a human subject in need thereof. In one embodiment, the subject is a human infant, for example one with one or more of NEC, low-birth weight, formula feeding, bacterial colonization of the gut, hypoxia, a condition associated with the release of HMGB1, a condition associated with the release of iNOS protein, or a condition associated with the release of RAGE, or a combination thereof.

Another embodiment relates to the administration of semapimod and/or guanylhydrazone containing compounds to decrease one or both of HMGB1 and iNOS protein expression to a subject in need thereof.

Another embodiment relates to the administration of semapimod and/or guanylhydrazone containing compounds to decrease RAGE to a subject in need thereof.

Semapimod has the following formula:

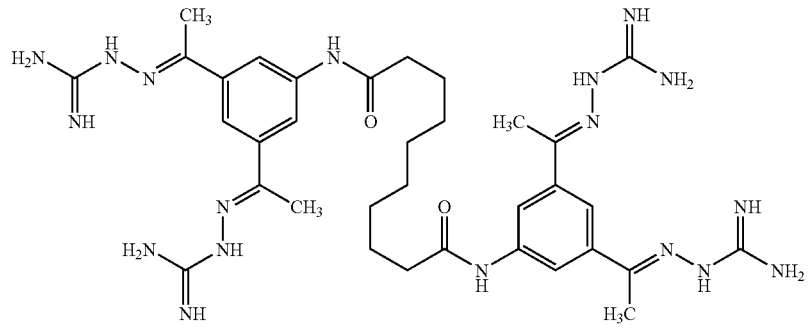

Other embodiments relates to methods and compositions that prevent or treat the conditions described herein. One embodiment relates to the use of guanylhydrazone ("Ghy", termed as an amidinohydrazone, i.e., (=N—NH—C (=NH)—NH$_2$) containing compounds and compositions. One embodiment relates to the use of aromatic guanylhydrazone-containing compounds and compositions.

One class of compounds useful for the purposes of the invention includes but is not limited to aromatics substituted with multiple guanylhydrazone (Ghy) moieties (i.e., amidinohydrazones). The synthesis and use of such compounds is described in U.S. Pat. No. 5,599,984 (the entire contents of which being hereby incorporated by reference) with respect to treating inflammatory conditions. The compounds can also be used in screening assays to test additional compounds for activity.

Other suitable guanylhydrazone compounds include those having the following formula:

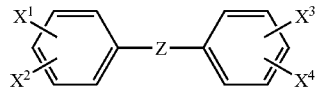

and/or salts thereof;

wherein $X^1$, $X^2$, $X^3$, and $X^4$ each independently represent H, GhyCH—, GhyCCH$_3$—, or CH$_3$CO—, with the provisos that $X^1$, $X^2$, $X^3$ and $X^4$ are not simultaneously H;

wherein Z is one or more selected from the group consisting of:

-(A$^1$)$_a$-(CR$^2$R$^3$)$_x$-(A$^2$)$_b$-;

-(A$^1$)$_a$-(CR$^2$R$^3$)$_x$-Q$_m$-(CR$^4$R$^5$)$_y$-(A$^2$)$_b$-; and

-(A$^1$)$_a$-(CR$^2$R$^3$)$_x$-Q$_m$-(CR$^4$R$^5$)$_y$-T$_n$(CR$^6$R$^7$)$_z$-(A$^2$)$_b$-;

and combinations thereof;

wherein a is selected from the group consisting of 0, 1, 2, 3, 4, 5, 6, 7, 8, and 9;

wherein b is selected from the group consisting of 0, 1, 2, 3, 4, 5, 6, 7, 8, and 9;

wherein x is selected from the group consisting of 0, 1, 2, 3, 4, 5, 6, 7, 8, and 9;

wherein y is selected from the group consisting of 0, 1, 2, 3, 4, 5, 6, 7, 8, and 9;

wherein z is selected from the group consisting of 0, 1, 2, 3, 4, 5, 6, 7, 8, and 9;

wherein m is selected from the group consisting of 0, 1, 2, 3, 4, 5, 6, 7, 8, and 9;

wherein n is selected from the group consisting of 0, 1, 2, 3, 4, 5, 6, 7, 8, and 9;

wherein $A^1$ and $A^2$ are each independently selected from the group consisting of —NR$^8$(CO)NR$^9$—, —(CO)NR$^8$—, —NR$^8$(CO)—, —NR$^8$—, —O—, —S—, —S(=O)—, —SO$_2$—, —SO$_2$NR$^8$—, —NR$^8$SO$_2$—, and salts thereof.

wherein Q and T are each independently selected from the group consisting of —NR$^{10}$(CO)NR$^{11}$—, —(CO)NR$^{10}$—, —NR$^{10}$(CO)—, —NR$^{10}$—, —O—, —S—, —S(=O)—, —SO$_2$—, —SO$_2$NR$^{10}$—, —NR$^{10}$SO$_2$—, salts thereof, branched or unbranched, saturated or unsaturated, substituted or unsubstituted C$_1$-C$_{20}$ alkylene, saturated or unsaturated, substituted or unsubstituted C$_3$-C$_{20}$ cycloalkylene, substituted or unsubstituted C$_5$-C$_{25}$ arylene, combinations thereof;

wherein one or more carbon atoms in any of said alkylene, cycloalkylene or arylene in said Q and/or T may each be independently replaced with one or more heteroatoms selected from the group consisting of nitrogen, oxygen, sulfur, and a combination thereof;

and wherein when substituted, each of said alkylene, cycloalkylene or arylene in said Q and/or T may be independently substituted with one or more substituent groups defined herein, and the substituent groups themselves may be optionally and independently substituted as defined herein. The R$^2$, R$^3$, R$^4$, R$^5$, R$^6$, R$^7$, R$^8$, R$^9$, R$^{10}$, and R$^{11}$ are defined herein, and may be optionally and independently substituted with one or more substituents defined herein. If desired, two independently chosen R$^2$, R$^3$, R$^4$, R$^5$, R$^6$, R$^7$, R$^8$, R$^9$, R$^{10}$, and R$^{11}$ alkyl-containing groups may be taken together with any atom to which they are attached to form a three to forty membered cyclic, heterocyclic or heteroaryl ring.

In the present application, GhyCH— is NH$_2$—(C(=NH)—NH—N=CH—; and GhyCH$_3$— is NH$_2$—C(=NH)—NH—N=CCH$_3$—.

In one embodiment, Z is a C$_1$-C$_{20}$ alkylene, which may be branched or unbranched, saturated or unsaturated, substituted or unsubstituted, and which may have one or more carbon atoms replaced by one or more heteroatoms selected from the group consisting of oxygen, nitrogen, sulfur, and a combination thereof. This includes alkylenes having 1, 2, 3, 4, 5, 6, 7, 8, 9, 10, 11, 12, 13, 14, 15, 16, 17, 18, 19, and 20 carbons.

In another embodiment, Z is a branched $C_1$-$C_{20}$ alkylene.

In another embodiment, Z is a unbranched $C_1$-$C_{20}$ alkylene.

In another embodiment, Z is a saturated $C_1$-$C_{20}$ alkylene.

In another embodiment, Z is a unsaturated $C_1$-$C_{20}$ alkylene.

In another embodiment, Z is a unsubstituted $C_1$-$C_{20}$ alkylene.

In another embodiment, Z is a substituted $C_1$-$C_{20}$ alkylene.

In another embodiment, Z is a $C_1$-$C_{20}$ alkylene in which one or more carbons is replaced with one or more heteroatoms selected from the group including oxygen, nitrogen, sulfur and a combination thereof.

In one embodiment, Z is a saturated or unsaturated, substituted or unsubstituted $C_3$-$C_{20}$ cycloalkylene, and which may have one or more carbon atoms replaced by one or more heteroatoms selected from the group consisting of oxygen, nitrogen, sulfur, and a combination thereof. This includes cycloalkylenes having 3, 4, 5, 6, 7, 8, 9, 10, 11, 12, 13, 14, 15, 16, 17, 18, 19, and 20 carbons.

In another embodiment, Z is a saturated $C_3$-$C_{20}$ cycloalkylene.

In another embodiment, Z is a unsaturated $C_3$-$C_{20}$ cycloalkylene.

In another embodiment, Z is a unsubstituted $C_3$-$C_{20}$ cycloalkylene.

In another embodiment, Z is a substituted $C_3$-$C_{20}$ cycloalkylene.

In another embodiment, Z is a $C_3$-$C_{20}$ cycloalkylene in which one or more carbons is replaced with one or more heteroatoms selected from the group including oxygen, nitrogen, sulfur and a combination thereof.

In one embodiment, Z is a substituted or unsubstituted $C_5$-$C_{25}$ arylene, wherein one or more carbon atoms in the cycloalkylene and arylene may be replaced with one or more heteroatoms selected from the group consisting of nitrogen, oxygen, sulfur, and a combination thereof. This includes arylenes having 6, 7, 8, 9, 10, 11, 12, 13, 14, 15, 16, 17, 18, 19, 20, 21, 22, 23, 24, and 25 carbons.

In another embodiment, Z is a substituted $C_5$-$C_{25}$ arylene.

In another embodiment, Z is a unsubstituted $C_5$-$C_{25}$ arylene.

In another embodiment, Z is a $C_5$-$C_{25}$ arylene in which one or more carbons is replaced with one or more heteroatoms selected from the group including oxygen, nitrogen, sulfur and a combination thereof.

In one embodiment, Z is an —NR$^8$(CO)NR$^9$— group, optionally in the salt form, wherein the R groups are both hydrogen.

In another embodiment, Z is a —($C_6H_4$)— group.

In another embodiment, Z is a —($CH_2$)$_p$— group, wherein p is 1, 2, 3, 4, 5, 6, 7, 8, 9, or 10.

In another embodiment, Z is a —($C_5H_3N$)— group.

In another embodiment, Z is a —O—($CH_2$)$_p$—O— group, wherein p is 1, 2, 3, 4, 5, 6, 7, 8, 9, or 10.

In another embodiment, Z is a -A-($CH_2$)$_p$-A- group, wherein p is 1, 2, 3, 4, 5, 6, 7, 8, 9, or 10, and wherein the A's are each independently —NH(CH)—, —(CO)NH—, or —NH(CO)NH— groups.

In another embodiment, Z is a -A-($C_6H_4$)-A- wherein the A's are each independently —CO—, —NH(CO)—, —(CO)NH—, or —NH(CO)NH— groups.

In another embodiment, Z is —O—($C_6H_4$)—O—, wherein the two "—O—" groups are para to each other the phenylene ring.

In another embodiment, Z is —O—($C_6H_4$)—O—, wherein the two "—O—" groups are meta to each other the phenylene ring.

In another embodiment, Z is —O—$CH_2$—$CH_2$—O—$CH_2$—$CH_2$—O—.

In another embodiment, Z is a group having the formula:

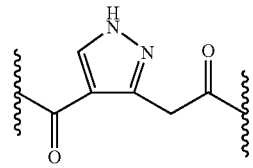

In another embodiment, Z is a group having the formula:

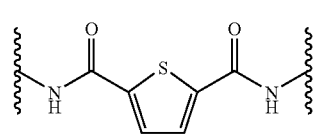

In another embodiment, Z is a group having the formula:

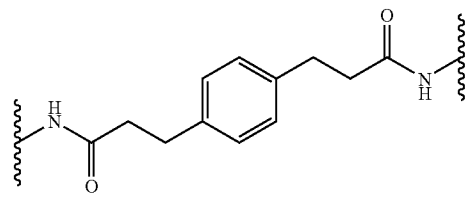

In another embodiment, Z is a group having the formula:

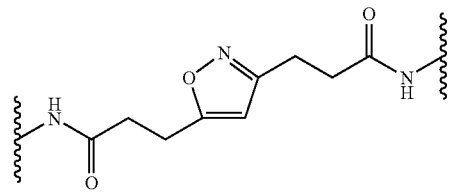

In another embodiment, Z is a group having the formula:

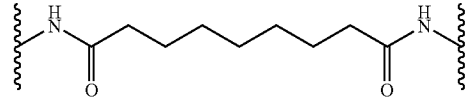

In another embodiment, Z is a group having the formula:

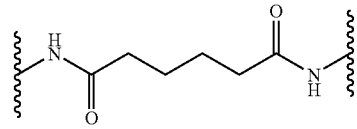

In another embodiment, Z is a group having the formula:

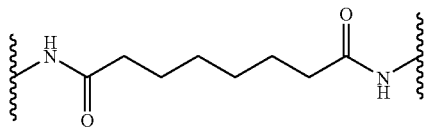

In another embodiment, Z is a group having the formula:

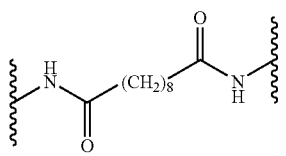

In one embodiment, the compound includes the structure:

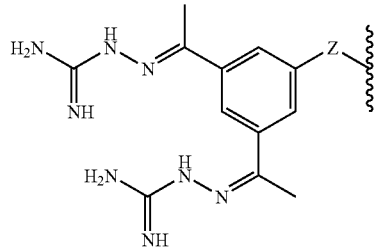

In one embodiment, the compound includes the structure:

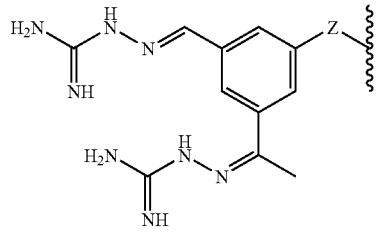

In one embodiment, the compound includes the structure:

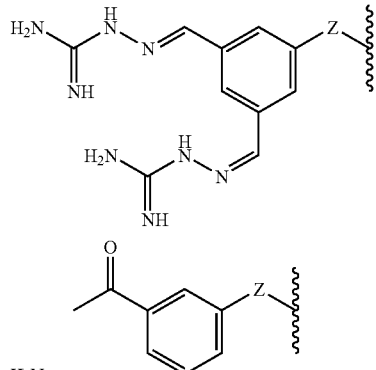

In one embodiment, the compound includes the structure:

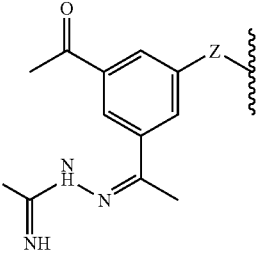

In one embodiment, the compound includes the structure:

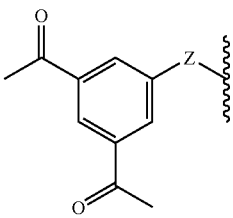

In one embodiment, the compound includes the structure:

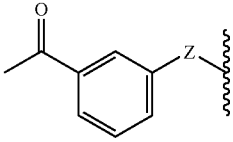

In one embodiment, the compound includes the structure:

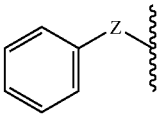

In one embodiment, the compound includes the structure:

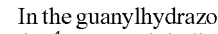

In one embodiment, the compound includes the structure:

In the guanylhydrazone containing compound, $X^1$, $X^2$, $X^3$, and $X^4$ may each individually adopt the ortho, meta or para position on the phenylene ring relative to the Z group. In another embodiment, the $X^1$, $X^2$, $X^3$, and $X^4$ are meta or para to the Z group. In another embodiment, the non-H $X^1$, $X^2$, $X^3$, and $X^4$ groups are meta to both the Z group and to each other.

As used herein, the formula "—NH(CO)—" includes the "—(CO)NH—" isomer.

In one embodiment, at least one of $X^1$, $X^2$, $X^3$ and $X^4$ is GhyCH— or GhyCCH$_3$—, $X^1$ and $X^2$ are not simultaneously H, and $X^3$ and $X^4$ are not simultaneously H.

In another embodiment, $X^1$, $X^2$, $X^3$, and $X^4$ are selected from the group including GhyCH— or GhyCCH$_3$—.

In another embodiment, $X^1$, $X^2$, $X^3$, and $X^4$ are selected from the group including GhyCH— or GhyCCH$_3$—, or CH$_3$CO—.

In another embodiment, $X^1$, $X^2$, $X^3$, and $X^4$ are each GhyCH—.

In another embodiment, $X^1$, $X^2$, $X^3$, and $X^4$ are each GhyCCH$_3$—.

In another embodiment, $X^1$, $X^2$, $X^3$, and $X^4$ are each CH$_3$CO—.

In another embodiment, at least one of $X^1$, $X^2$, $X^3$, and $X^4$ is CH$_3$CO—.

In another embodiment, the compound is in the salt form. p In another embodiment, the compound is in the salt form having a compound:salt ratio of 1:1, 1:2, 1:3, 1:4 or 2:1.

In one embodiment, Z has the formula:

$$-(A^1)_a\text{-}(CR^2R^3)_x\text{-}Q_m\text{-}(CR^4R^5)_y\text{-}T_n\text{-}(CR^6R^7)_z\text{-}(A^2)_b\text{-};$$

wherein each of the variables a, m, n, and b are equal to 1; and the sum of the variables x, y and z does not exceed 12; and wherein Q, T, $A^1$, $R^2$, $R^3$, $R^4$, $R^5$, $R^6$, $R^7$, $A^2$, $R^{10}$, and $R^{11}$ are defined herein.

In one embodiment, Z has the formula:

$$-(A^1)_a\text{-}(CR^2R^3)_x\text{-}Q_m\text{-}(CR^4R^5)_y\text{-}T_n\text{-}(CR^6R^7)_z\text{-}(A^2)_b\text{-};$$

wherein each of the variables, a, m, n, and b are equal to 1; and the sum of the variables x, y and z does not exceed 12;

wherein Q and T are each independently selected from the group consisting $R^{10}(CO)NR^{11}$—, —(CO)NR$^{10}$—, —NR$^{10}$(CO)—, —NR$^{10}$—, salts thereof, —O—, optionally substituted alkylene, optionally substituted arylene, optionally substituted heteroarylene, and combinations thereof;

and wherein $A^1$, $R^2$, $R^3$, $R^4$, $R^5$, $R^6$, $R^7$, $A^2$, $R^{10}$, and $R^{11}$ are defined herein.

In one embodiment, Z has the formula:

$$-(A^1)_a\text{-}(CR^2R^3)_x\text{-}Q_m\text{-}(CR^4R^5)_y\text{-}T_n\text{-}(CR^6R^7)_z\text{-}(A^2)_b\text{-};$$

wherein each of the variables, a, m, n, and b are equal to 1; and the sum of the variables x, y and z does not exceed 12;

wherein Q and T are each independently selected from the group consisting $R^{10}(CO)NR^{11}$—, —(CO)NR$^{10}$—, —NR$^{10}$(CO)—, —NR$^{10}$—, salts thereof, —O—, optionally substituted alkylene, optionally substituted arylene, optionally substituted heteroarylene, and combinations thereof;

and wherein $A^1$, $R^2$, $R^3$, $R^4$, $R^5$, $R^6$, $R^7$, $A^2$, $R^{10}$, and $R^{11}$ are defined herein.

with the proviso that if Q is —NR$^{10}$— or —O— and y is 1 then T is not —NR$^{10}$— or —O—.

In one embodiment, Z has the formula:

$$-(A^1)_a\text{-}(CR^2R^3)_x\text{-}Q_m\text{-}(CR^4R^5)_y\text{-}T_n\text{-}(CR^6R^7)_z\text{-}(A^2)_b\text{-};$$

wherein each of the variables, a, m, n, and b are equal to 1; and the sum of the variables x, y and z does not exceed 12;

wherein Q and T are each independently selected from the group consisting $R^{10}(CO)NR^{11}$—, —(CO)NR$^{10}$—, —NR$^{10}$(CO)—, —NR$^{10}$—, salts thereof, —O—, optionally substituted alkylene, optionally substituted arylene, optionally substituted heteroarylene, and combinations thereof;

and wherein $A^1$, $R^2$, $R^3$, $R^4$, $R^5$, $R^6$, $R^7$, $A^2$, $R^{10}$, and $R^{11}$ are defined herein.

with the proviso that if Q is —NR$^{10}$— or —O— and y is 1 then T is not —NR$^{10}$— or —O—;

and with the proviso that if Q is —(CO)NR$^{10}$—, —NR$^{10}$(CO)—, —NR$^{10}$—, or —O— and y is 1 then T is not —(CO)NR$^{10}$—, —NR$^{10}$(CO)—, —NR$^{10}$—, or —O—.

In one embodiment, Z has the formula:

$$-(A^1)_a\text{-}(CR^2R^3)_x\text{-}Q_m\text{-}(CR^4R^5)_y\text{-}T_n\text{-}(CR^6R^7)_z\text{-}(A^2)_b\text{-};$$

wherein Q and T are each independently selected from the group consisting $R^{10}(CO)NR^{11}$—, —(CO)NR$^{10}$—, —NR$^{10}$(CO)—, —NR$^{10}$—, salts thereof, —O—, optionally substituted alkylene, optionally substituted arylene, optionally substituted heteroarylene, and combinations thereof;

wherein $A^1$, $R^2$, $R^3$, $R^4$, $R^5$, $R^6$, $R^7$, $A^2$, $R^{10}$, and $R^{11}$ are defined herein.

wherein if substituted, the alkylene, arylene, and/or heteroarylene are each independently substituted with 0 to 4 groups selected from the group consisting of H, halogen, OR, NR$^1$R$^{1'}$, NR$^1$CO, CONR$^1$, COR$^1$, SO$_2$R$^1$, SO$_2$NR$^1$, SOR$^1$, alkyl, aryl, heteroalkyl, and heteroaryl, salts thereof, and combinations thereof.

$R^1$ and $R^{1'}$ being each independently selected from the group including hydrogen, hydroxy, halo, bromo, chloro, iodo, fluoro, —N$_3$, —CN, —NC, —SH, —NO$_2$, —NH$_2$, (C$_1$-C$_{20}$)alkyl, phenyl, (C$_3$-C$_{20}$)cycloalkyl, (C$_1$-C$_{20}$)alkoxy, (C$_3$-C$_{25}$)heteroaryl, (C$_3$-C$_{25}$)heterocyclic, (C$_2$-C$_{20}$)alkenyl, (C$_3$-C$_{20}$)cycloalkenyl, (C$_2$-C$_{20}$)alkynyl, (C$_5$-C$_{20}$)cycloalkynyl, (C$_5$-C$_{25}$)aryl, perhalo(C$_1$-C$_{20}$)alkyl, C$_1$-C$_{20}$)alkyl-O—, phenyl-O—, (C$_3$-C$_{20}$)cycloalkyl-O—, (C$_3$-C$_{25}$)heteroaryl-O—, (C$_3$-C$_{25}$)heterocyclic-O—, (C$_2$-C$_{20}$)alkenyl-O—, (C$_3$-C$_{20}$) cycloalkenyl-O—, (C$_3$-C$_{20}$)alkynyl-O—, (C$_5$-C$_{20}$)cycloalkynyl-O—, (C$_5$-C$_{25}$)aryl-O—, perhalo(C$_1$-C$_{20}$)alkyl-O—, (C$_1$-C$_{20}$)alkyl-S—, phenyl-S-, (C$_3$-C$_{20}$)cycloalkyl-S—, (C$_3$-C$_{25}$)heteroaryl-S—, (C$_3$-C$_{25}$)heterocyclic-S—, (C$_2$-C$_{20}$)alkenyl-S—, (C$_3$-C$_{20}$)cycloalkenyl-S—, (C$_2$-C$_{20}$)alkynyl-S—, (C$_5$-C$_{20}$)cycloalkynyl-S—, (C$_5$-C$_{25}$)aryl-S—, perhalo (C$_1$-C$_{20}$)alkyl-S—, (C$_1$-C$_{20}$)alkyl-SO$_2$—, phenyl-SO$_2$—, (C$_3$-C$_{20}$)-SO$_2$—, (C$_1$-C$_{20}$)alkoxy-SO$_2$—, (C$_3$-C$_{25}$)heteroaryl-SO$_2$, (C$_3$-C$_{25}$)heterocyclic-SO$_2$—, (C$_2$-C$_{20}$)alkenyl-SO$_2$—, (C$_3$-C$_{20}$)cycloalkenyl-SO$_2$—, (C$_2$-C$_{20}$)alkynyl-SO$_2$—, (C$_5$-C$_{20}$)cycloalkynyl-SO$_2$—, (C$_5$-C$_{25}$)aryl-SO$_2$—, perhalo(C$_1$-C$_{20}$)alkyl-SO$_2$—, H$_2$N—SO$_2$—, (C$_1$-C$_{20}$)alkyl-NH—SO$_2$—, phenyl-NH—SO$_2$—, (C$_3$-C$_{20}$)cycloalkyl-NH—SO$_2$, (C$_1$-C$_{20}$)alkoxy-NH—SO$_2$—, (C$_3$-C$_{25}$)heteroaryl-SO$_2$—, (C$_3$-C$_{25}$)heterocyclic-NH—SO$_2$—, (C$_2$-C$_{20}$)alkenyl-NH—SO$_2$—, (C$_3$-C$_{20}$)cycloalkenyl-NH—SO$_2$—, (C$_2$-C$_{20}$)alkynyl-NH—SO$_2$—, (C$_5$-C$_{20}$)cycloalkynyl-NH—SO$_2$—, (C$_5$-C$_{25}$)aryl-NH—SO$_2$—, perhalo(C$_1$-C$_{20}$)alkyl-NH—SO$_2$—, {(C$_1$-C$_{20}$)alkyl}$_2$N—SO$_2$—, {phenyl}$_2$N—SO$_2$—, {(C$_3$-C$_{20}$)cycloalkyl}$_2$N—SO$_2$—, {(C$_1$-C$_{20}$)alkoxy}$_2$N—SO$_2$—, {(C$_3$-C$_{25}$)heteroaryl}$_2$N—SO$_2$—, {(C$_3$-C$_{25}$)heterocyclic}$_2$N—SO$_2$—, {(C$_2$-C$_{20}$)alkenyl}$_2$N—SO$_2$—, {(C$_2$-C$_{20}$)alkynyl}$_2$N—SO$_2$—, {C$_5$-C$_{20}$)cycloalkynyl}$_2$N—SO$_2$—, {(C$_5$-C$_{25}$)aryl}$_2$N—SO$_2$—, {perhalo(C$_1$-C$_{20}$)alkyl}$_2$N—SO$_2$—, C$_1$-C$_{20}$)alkyl-SO$_2$—NH—, phenyl-SO$_2$—NH—, (C$_3$-C$_{20}$)cycloalkyl-SO$_2$—NH—,(C$_1$-C$_{20}$)alkoxy-SO$_2$—NH—, (C$_3$-C$_{25}$)heteroaryl-SO$_2$—NH—, (C$_3$-C$_{25}$)heterocyclic-SO$_2$—NH—, (C$_2$-C$_{20}$)alkenyl-SO$_2$—NH—, (C$_3$-C$_{20}$)cycloalkenyl-SO$_2$—NH—, (C$_2$-C$_{20}$)alkynyl-SO$_2$—NH—, (C$_5$-C$_{20}$)cycloalkynyl-SO$_2$—NH—, (C$_5$-C$_{25}$)aryl-SO$_2$—NH—, perhalo(C$_1$-C$_{20}$)alkyl-SO$_2$—NH—, (C$_1$-C$_{20}$)alkyl-NH—, phenyl-NH—, (C$_3$-C$_{20}$)cycloalkyl-NH—, (C$_1$-C$_{20}$)alkoxy-NH—, (C$_3$-C$_{25}$)heteroaryl-NH—, (C$_3$-C$_{25}$)heterocyclic-NH—, (C$_2$-C$_{20}$)alkenyl-NH—, (C$_3$-C$_{20}$) cycloalkenyl-NH—, (C$_2$-C$_{20}$)alkynyl-NH—, (C$_5$-C$_{20}$)cycloalkynyl-NH—, (C$_5$-C$_{25}$)aryl-NH —, perhalo(C$_1$-C$_{20}$)alkyl-NH—, {(C$_1$-C$_{20}$)alkyl}$_2$N—, {phenyl}$_2$N—, {(C$_3$-C$_{20}$cycloalkyl}$_2$N—, {(C$_1$-C$_{20}$)alkoxy}$_2$N—, {(C$_3$-C$_{25}$)heteroaryl}$_2$N—, {(C$_3$-C$_{25}$)

heterocyclic}$_2$N—, {(C$_2$-C$_{20}$)alkenyl}$_2$N—, {(C$_3$-C$_{20}$)cycloalkenyl}$_2$N—, {(C$_2$-C$_{20}$)alkynyl}$_2$N—, {(C$_5$-C$_{20}$)cycloalkynyl}$_2$N—, {(C$_5$-C$_{25}$aryl}$_2$N—, {perhalo(C$_1$-C$_{20}$)alkyl}$_2$N—, (C$_1$-C$_{20}$)alkyl-(C=O)—NH—, phenyl-(C=O)—NH—, (C$_3$-C$_{20}$)cycloalkyl-(C=O)—NH—, (C$_1$-C$_{20}$)alkoxy-(C=O)—NH—, (C$_3$-C$_{25}$)heteroaryl-(C=O)—NH—, (C$_3$-C$_{25}$)heterocyclic-(C=O)—NH—, (C$_2$-C$_{20}$)alkenyl-(C=O)—NH—, (C$_3$-C$_{20}$)cycloalkenyl-(C=O)—NH—, (C$_2$-C$_{20}$)alkynyl-(C=O)—NH—, (C$_5$-C$_{20}$)cycloalkynyl-(C=O)—NH—, (C$_5$-C$_{25}$)aryl-(C=O)—NH—, perhalo(C$_1$-C$_{20}$)alkyl-(C=O—NH—, (C$_1$-C$_{20}$)alkyl-(C=O)-{((C$_1$-C$_{20}$)alkyl)N}—, phenyl-(C=O)-{((C$_1$-C$_{20}$)alkyl)N}—, (C$_3$-C$_{20}$)cycloalkyl-(C=O)-{((C$_1$-C$_{20}$)alkyl)N}—, (C$_1$-C$_{20}$)alkoxy-(C=O)-{((C$_1$-C$_{20}$)alkyl)N}—, (C$_3$-C$_{25}$)heteroaryl-(C=O)-{((C$_1$-C$_{20}$)alkyl)N}—, (C$_3$-C$_{25}$)heterocyclic-(C=O)-{((C$_1$-C$_{20}$)alkyl)N}—, (C$_2$-C$_{20}$)alkenyl-(C=O)-{((C$_1$-C$_{20}$)alkyl)N}—, (C$_3$-C$_{20}$)cycloalkenyl-(C=O)-{((C$_1$-C$_{20}$)alkyl)N}—, (C$_2$-C$_{20}$)alkynyl-(C=O)-{((C$_1$-C$_{20}$)alkyl)N}—, (C$_5$-C$_{20}$)cycloalkynyl-(C=O)-{((C$_1$-C$_{20}$)alkyl)N}—, (C$_5$-C$_{25}$)aryl-(C=O)-{((C$_1$-C$_{20}$)alkyl)N}—, perhalo(C$_1$-C$_{20}$)alkyl-(C=O)-{((C$_1$-C$_{20}$)alkyl)N}—, phenyl-(C=O)—NH—, phenyl-(C=O)-{(phenyl)N}—, (C$_1$-C$_{20}$)alkyl-(C=O)-{(phenyl)N}—, (C$_3$-C$_{20}$)cycloalkyl-(C=O)-{(phenyl)N}—, (C$_1$-C$_{20}$)alkoxy-(C=O)-{(phenyl)N}—, (C$_3$-C$_{25}$)heteroaryl-(C=O)-{(phenyl)N}—, (C$_3$-C$_{25}$)heterocyclic-(C=O)-{(phenyl)N}—, (C$_2$-C$_{20}$)alkenyl-(C=O)-{(phenyl)N}—, (C$_3$-C$_{20}$)cycloalkenyl-(C=O)-{(phenyl)N}—, (C$_2$-C$_{20}$)alkynyl-(C=O)-{(phenyl)N}—, (C$_3$-C$_{20}$)cycloalkynyl-(C=O)-{(phenyl)N}—, (C$_5$-C$_{25}$)aryl-(C=O)-{(phenyl)N}—, perhalo(C$_1$-C$_{20}$)alkyl-(C=O)-{(phenyl)N}—, H$_2$N(C=O)—, (C$_1$-C$_{20}$)alkyl-NH—(C=O)—, phenyl-NH—(C=)—, (C$_3$-C$_{20}$)cycloalkyl-NH—(C=O)—, (C$_1$-C$_{20}$)alkoxy-NH—(C=O)—, (C$_3$-C$_{25}$)heteroaryl-NH—(C=O)—, (C$_3$-C$_{25}$)heterocyclic-NH—(C=O)—, (C$_2$-C$_{20}$)alkenyl-NH—(C=O)—, (C$_3$-C$_{20}$)cycloalkenyl-NH-(C=O)—, (C$_2$-C$_{20}$)alkynyl-NH—(C=O)—, (C$_5$-C$_{20}$)cycloalkynyl-NH—(C=O)—, (C$_5$-C$_{25}$)aryl-NH—(C=O)—, perhalo(C$_1$-C$_{20}$)alkyl-NH—(C=O)—, {C$_1$-C$_{20}$)alkyl}$_2$N—(C=O)—, {phenyl}{(C$_1$-C$_{20}$)alkyl}N—(C=O)—, {(C$_3$-C$_{20}$)cycloalkyl}{(C$_1$-C$_{20}$)alkyl}N—(C=O)—, {(C$_1$-C$_{20}$)alkoxy}{(C$_1$-C$_{20}$)alkyl}N—(C=O—, {(C$_3$-C$_{25}$)heteroaryl}{(C$_1$-C$_{20}$)alkyl}N—(C=O)—, {(C$_3$-C$_{25}$)heterocyclic}{(C$_1$-C$_{20}$)alkyl}N—(C=O)—, {(C$_2$-C$_{20}$)alkenyl}{(C$_1$-C$_{20}$)alkyl}N—(C=O)—, {(C$_3$-C$_{20}$)cycloalkenyl}{(C$_1$-C$_{20}$)alkyl}N—(C=O)—, {(C$_2$-C$_{20}$)alkynyl}{(C$_1$-C$_{20}$)alkyl}N—(C=O)—, {(C$_5$-C$_{20}$)cycloalkynyl}{(C$_1$-C$_{20}$)alkyl}N—(C=O)—, {(C$_5$-C$_{25}$)aryl}{(C$_1$-C$_{20}$)alkyl}N—(C=O)—, {perhalo(C$_1$-C$_{20}$)alkyl}{(C$_1$-C$_{20}$)alkyl}N—(C=O)—, {phenyl}$_2$N—(C=O)—, {(C$_3$-C$_{20}$)cycloalkyl}{phenyl}N—(C=O)—, {(C$_1$-C$_{20}$)alkoxy}{phenyl}N—(C=O)—, {(C$_3$-C$_{25}$)heteroaryl}{phenyl}N—(C=O)—, {(C$_3$-C$_{25}$)heterocyclic}{phenyl}N—(C=O)—, {(C$_2$-C$_{20}$)alkenyl}{phenyl}N—(C=O)—, {(C$_3$-C$_{20}$)cycloalkenyl}{phenyl}N—(C=O)—, {(C$_2$-C$_{20}$)alkynyl}{phenyl}N—(C=O)—, {(C$_5$-C$_{20}$)cycloalkynyl}{phenyl}N—(C=O)—, {(C$_5$-C$_{25}$)aryl}{phenyl}N—(C=O)—, {perhalo(C$_1$-C$_{20}$)alkyl}{phenyl}N—(C=O)—, HO—(C=O)—, (C$_1$-C$_{20}$)alkyl-(C=O)—, (C$_3$-C$_{25}$)heteroaryl-(C=O)—, (C$_3$-C$_{25}$)heterocyclic-(C=O)—, (C$_2$-C$_{20}$)alkenyl-(C=O)—, (C$_3$-C$_{20}$)cycloalkenyl-(C=O)—, (C$_2$-C$_{20}$)alkynyl-(C=O)—, (C$_5$-C$_{25}$)aryl-(C=O)—, perhalo(C$_1$-C$_{20}$)alkyl-(C=O)—, phenyl-(C=O)—, (C$_1$-C$_{20}$)alkyl-O—(C=O)—, (C$_3$-C$_{25}$)heteroaryl-O—(C=O)—, (C$_3$-C$_{25}$)heterocyclic-O—(C=O)—, (C$_2$-C$_{20}$)alkenyl-O—(C=O)—, (C$_3$-C$_{20}$)cycloalkenyl-O—(C=O)—, (C$_2$-C$_{20}$)alkynyl-O—(C=O)—, (C$_5$-C$_{25}$)aryl-O—(C=O)—, perhalo(C$_1$-C$_{20}$)alkyl-O—(C=O)—, phenyl-O—(C=O)—, (C$_1$-C$_{20}$)alkyl-(C=O)—O—, (C$_3$-C$_{25}$)heteroaryl-(C=O)—O—, (C$_3$-C$_{25}$)heterocyclic-(C=O)—O—, (C$_2$-C$_{20}$)alkenyl-(C=O)—O—, (C$_3$-C$_{20}$)cycloalkenyl-(C=O)—O—, (C$_2$-C$_{20}$)alkynyl-(C=O)—O—, (C$_5$-C$_{25}$)aryl-(C=O)—O—, phenyl-(C=O)—O—, perhalo(C$_1$-C$_{20}$)alkyl-(C=O)—O—, and salts thereof;

wherein each of the aforesaid (C$_1$-C$_{20}$)alkyl, phenyl, (C$_3$-C$_{20}$)cycloalkyl, (C$_1$-C$_{20}$)alkoxy, C$_3$-C$_{25}$)heterocyclic, (C$_2$-C$_{20}$)alkenyl, (C$_3$-C$_{20}$)cycloalkenyl, (C$_2$-C$_{20}$)alkynyl, (C$_5$-C$_{20}$)cycloalkynyl, and (C$_5$-C$_{25}$)aryl groups (of the R$^1$ and R$^{1'}$ groups) may be optionally and independently substituted by one to four moieties selected from the group consisting of hydroxy, halo, bromo, chloro, iodo, fluoro, —N$_3$, —CN, —NC, —SH, —NO$_2$, —NH$_3$, (C$_1$-C$_{20}$)alkyl, phenyl, (C$_3$-C$_{20}$)cycloalkyl, (C$_1$-C$_{20}$)alkoxy, (C$_3$-C$_{25}$)heteroaryl, (C$_3$-C$_{25}$)heterocyclic, (C$_2$-C$_{20}$)alkenyl, (C$_3$-C$_{20}$)cycloalkenyl, (C$_2$-C$_{20}$)alkynyl, (C$_5$-C$_{20}$)cycloalkynyl, (C$_5$-C$_{25}$)aryl, perhalo(C$_1$-C$_{20}$)alkyl, (C$_1$-C$_{20}$)alkyl-O—, phenyl-O—, (C$_3$-C$_{20}$)cycloalkyl-O—, (C$_3$-C$_{25}$)heteroaryl-O—, (C$_3$-C$_{25}$)heterocyclic-O—, (C$_2$-C$_{20}$)alkenyl-O—, (C$_3$-C$_{20}$)cycloalkenyl-O—, (C$_2$-C$_{20}$)alkynyl-O—, (C$_5$-C$_{20}$)cycloalkynyl-O—, (C$_3$-C$_{25}$)aryl-O—, perhalo(C$_1$-C$_{20}$)alkyl, (C$_1$-C$_{20}$)alkyl-S—, phenyl-S—, (C$_3$-C$_{20}$)cycloalkyl-S—, (C$_3$-C$_{25}$)heteroaryl-S—, (C$_3$-C$_{25}$)heterocyclic-S—, (C$_2$-C$_{20}$)alkenyl-S—, (C$_3$-C$_{20}$)cycloalkenyl-S—, (C$_2$-C$_{20}$)alkynyl-S—, (C$_5$-C$_{20}$)cycloalkynyl-S—, (C$_5$-C$_{25}$)aryl-S—, perhalo(C$_1$-C$_{20}$)alkyl-S—, (C$_1$-C$_{20}$)alkyl-SO$_2$—, phenyl-SO$_2$—, (C$_3$-C$_{20}$)cycloalkyl-SO$_2$—, (C$_1$-C$_{20}$)alkoxy-SO$_2$—, (C$_3$-C$_{25}$)heteroaryl-SO$_2$—, (C$_3$-C$_{25}$)heterocyclic-SO$_2$—, (C$_2$-C$_{20}$)alkenyl-SO$_2$—, (C$_3$-C$_{20}$)cycloalkenyl-SO$_2$—, (C$_2$-C$_{20}$)alkynyl-SO$_2$)—, (C$_5$-C$_{20}$)cycloalkynyl-SO$_2$, (C$_5$-C$_{25}$)aryl-SO$_2$—, perhalo(C$_1$-C$_{20}$)alkyl-SO$_2$—, H$_2$N—SO$_2$—, (C$_1$-C$_{20}$)alkyl-NH—SO$_2$—, phenyl-NH—SO$_2$—, (C$_3$-C$_{20}$)cycloalkyl-NH—SO$_2$—, (C$_1$-C$_{20}$)alkoxy-NH—SO$_2$—, (C$_3$-C$_{25}$)heteroaryl-NH—O$_2$—, (C$_3$-C$_{25}$)heterocyclic-NH—SO$_2$—, (C$_2$-C$_{20}$)alkenyl-NH—SO$_2$—, (C$_3$-C$_{20}$cycloalkenyl-NH—SO$_2$—, (C$_2$-C$_{20}$)alkenyl-NH—SO$_2$—, (C$_5$-C$_{20}$)cycloalkynyl-NH—SO$_2$—, (C$_5$-C$_{25}$)aryl-NH—SO$_2$—, perhalo(C$_1$C$_{20}$)alkyl-NH—SO$_2$—, {(C$_1$-C$_{20}$)alkyl}$_2$N—SO$_2$—, {phenyl}$_2$N—SO$_2$, {(C$_3$-C$_{20}$)cycloalkyl}$_2$N—SO$_2$—, {(C$_1$-C$_{20}$)alkoxy}$_2$N—SO$_2$—, {(C$_3$-C$_{25}$)heteroaryl}$_2$N—SO$_2$—, {(C$_3$-C$_{25}$)heterocyclic}$_2$N—SO$_2$—, {(C$_2$-C$_{20}$)alkenyl}$_2$N—SO$_2$—, {(C$_2$-C$_{20}$)alkynyl}$_2$N—SO$_2$—, {(C$_5$-C$_{20}$)cycloalkynyl}$_2$N—SO$_2$—, {(C$_5$-C$_{25}$)aryl}$_2$N—SO$_2$—, {perhalo(C$_1$-C$_{20}$)alkyl}$_2$N—SO$_2$—, (C$_1$-C$_{20}$)alkyl-SO$_2$—NH—, phenyl-SO$_2$—NH—, (C$_3$-C$_{20}$)cycloalkynyl-SO$_2$—NH—, (C$_1$-C$_{20}$)alkoxy-SO$_2$—NH—, (C$_3$-C$_{25}$)heteroaryl-SO$_2$—NH—, (C$_3$-C$_{25}$)heterocyclic-SO$_2$—NH—, (C$_2$-C$_{20}$)alkenyl-SO$_2$—NH—, (C$_3$-C$_{20}$)cycloalkenyl-SO$_2$—NH—, (C$_2$-C$_{20}$)alkynyl-SO$_2$—NH—, (C$_5$-C$_{20}$)cycloalkynyl-SO$_2$—NH—, (C$_5$-C$_{25}$)aryl-SO$_2$—NH—, perhalo(C$_1$-C$_{20}$)alkyl-SO$_2$—NH—, (C$_1$-C$_{20}$)alkyl-NH—, phenyl-NH—, (C$_3$-C$_{20}$)cycloalkyl-NH—, (C$_1$-C$_{20}$)alkoxy-NH—, (C$_3$-C$_{25}$)heteroaryl-NH—, (C$_3$-C$_{25}$)heterocyclic-NH—, (C$_2$-C$_{20}$)alkenyl-NH—, (C$_3$-C$_{20}$)cycloalkenyl-NH—, (C$_2$-C$_{20}$)alkynyl-NH—, (C$_5$-C$_{20}$)cycloalkynyl-NH—, (C$_5$-C$_{25}$)aryl-NH—, perhalo(C$_1$-C$_{20}$)alkyl-NH—, {(C$_1$-C$_{20}$)alkyl}$_2$N—, {phenyl}$_2$N—, {(C$_3$-C$_{20}$)cycloalkyl}$_2$N—, {(C$_1$-C$_{20}$)alkoxy}$_2$N—, {(C$_3$-C$_{25}$)heteroaryl}$_2$N—, {(C$_3$-C$_{25}$)heterocyclic}$_2$N—, {(C$_2$-C$_{20}$)alkenyl}$_2$N—, {(C$_3$-C$_{20}$)cycloalkenyl}$_2$N—, {(C$_2$-C$_{20}$)alkynyl}$_2$N—, {(C$_5$-C$_{20}$)cycloalkynyl}$_2$N—, {(C$_5$-C$_{25}$)aryl}$_2$N—, {perhalo(C$_1$-C$_{20}$)alkyl}$_2$N—, (C$_1$-C$_{20}$)alkyl-(C=O)—NH—, phenyl-(C=O)—NH—, (C$_3$-C$_{20}$)

cycloalkyl-(C=O)—NH—, (C$_1$-C$_{20}$)alkoxy-(C=O)—NH—, (C$_3$-C$_{25}$)heteroaryl-(C=O)—NH—, (C$_3$-C$_{25}$)heterocyclic-(C=O)—NH—, (C$_2$-C$_{20}$)alkenyl-(C=O)—NH—, (C$_3$-C$_{20}$)cycloalkenyl-(C=O)—NH—, (C$_2$-C$_{20}$)alkynyl-(C=O)—NH—, (C$_5$-C$_{20}$)cycloalkynyl-(C=O)—NH—, (C$_5$-C$_{25}$)aryl-(C=O)—NH—, perhalo(C$_1$-C$_{20}$)alkyl-(C=O)—NH—, (C$_1$-C$_{20}$)alkyl-(C=O)-{((C$_1$-C$_{20}$)alkyl)N}—, phenyl-(C=O)-{((C$_1$-C$_{20}$)alkyl)N}6—, (C$_3$-C$_{20}$)cycloalkyl-(C=O)-{((C$_1$-C$_{20}$)alkyl)N}—, (C$_1$-C$_{20}$)alkoxy-(C=O)-{((C$_1$-C$_{20}$)alkyl)N}—, (C$_3$-C$_{25}$)heteroaryl-(C=O)-{((C$_1$-C$_{20}$)alkyl)N}—, (C$_3$-C$_{25}$)heterocyclic-(C=O)-{((C$_1$-C$_{20}$)alkyl)N}—, (C$_2$-C$_{20}$)alkenyl-(C=O)-{((C$_1$-C$_{20}$)alkyl)N}—, (C$_3$-C$_{20}$)cycloalkenyl-(C=O)-{((C$_1$-C$_{20}$)alkyl)N}—, (C$_2$-C$_{20}$)alkynyl-(C=O)-{((C$_1$-C$_{20}$)alkyl)N}—, (C$_5$-C$_{20}$)cycloalkynyl-(C=O)-{((C$_1$-C$_{20}$)alkyl)N}—, (C$_5$-C$_{25}$)aryl-(C=O)-{((C$_1$-C$_{20}$)alkyl)N}—, perhalo(C$_1$-C$_{20}$)alkyl-(C=O)-{((C$_1$-C$_{20}$)alkyl)N}—, phenyl-(C=O)—NH, phenyl-(C=O)-{(phenyl)N}—, (C$_1$-C$_{20}$)alkyl-(C=O)-{(phenyl)N}—, (C$_3$-C$_{20}$)cycloalkyl-C(=O)-{(phenyl)N}—, (C$_1$-C$_{20}$)alkoxy-(C=O)-{(phenyl)N}—, (C$_3$-C$_{25}$)heteroaryl-(C=O)-{(phenyl)N}—, (C$_3$-C$_{25}$)heterocyclic-(C=O)-{(phenyl)N}—, (C$_2$-C$_{20}$)alkenyl-(C=O)-{(phenyl)N}—, (C$_3$-C$_{20}$)cycloalkenyl-(C=O)-{(phenyl)N}—, (C$_2$-C$_{20}$)alkynyl-(C=O)-{(phenyl)N}—, (C$_5$-C$_{20}$)cycloalkynyl-(C=O)-{(phenyl)N}—, (C$_5$-C$_{25}$)aryl-(C=O)-{(phenyl)N}—, perhalo(C$_1$-C$_{20}$)alkyl-(C=O)-{(phenyl)N}—, H$_2$N(C=O)—, (C$_1$-C$_{20}$)alkyl)NH-(C=)—, phenyl-NH—(C=O)—, (C$_3$-C$_{20}$)cycloalkyl-NH—(C=O)—, (C$_1$-C$_{20}$)alkoxy-NH-(C=O)—, (C$_3$-C$_{25}$)heteroaryl-NH—(C=O)—, (C$_3$-C$_{25}$)heterocyclic-(C=O)-NH—(C=O)—, (C$_2$-C$_{20}$)alkenyl-NH—(C=O)—, (C$_3$-C$_{20}$)cycloalkenyl-NH—(C=O)—, (C$_2$-C$_{20}$)alkynyl-NH—(C=O)—, (C$_5$-C$_{20}$)cycloalkynyl-NH—(C=O)—, (C$_5$-C$_{25}$)aryl-NH—(C=O)—, perhalo(C$_1$-C$_{20}$)alkyl-NH—(C=O)—, {C$_1$-C$_{20}$)alkyl}$_2$N—(C=O)—, {phenyl}{(C$_1$-C$_{20}$)alkyl}N—(C=O)—, {(C$_3$-C$_{20}$)cycloalkyl}{(C$_1$-C$_{20}$)alkyl}N—(C=O)—, {(C$_1$-C$_{20}$)alkoxy}{(C$_1$-C$_{20}$)alkyl}N—(C=O)—, {(C$_3$-C$_{25}$)heteroaryl}{(C$_1$-C$_{20}$)alkyl}N—(C=O)—, {(C$_3$-C$_{25}$)heterocyclic}{(C$_1$-C$_{20}$)alkyl}N—(C=O)—, {(C$_2$-C$_{20}$)alkenyl}{(C$_1$-C$_{20}$)alkyl}N—(C=O) —, {(C$_3$-C$_{20}$)cycloalkenyl}{(C$_1$-C$_{20}$)alkyl}N—(C=O)—, {(C$_2$-C$_{20}$)alkynyl}{(C$_1$-C$_{20}$)alkyl}N—(C=O)—, {(C$_5$-C$_{20}$)cycloalkynyl}{(C$_1$-C$_{20}$)alkyl}N—(C=O)—, {(C$_5$-C$_{25}$)aryl}{(C$_1$-C$_{20}$)alkyl}N—(C=O)—, {perhalo(C$_1$-C$_{20}$)alkyl}{(C$_1$-C$_{20}$)alkyl}N—(C=O)—, {phenyl}$_2$N—(C=O)—, {(C$_3$-C$_{20}$)cycloalkyl}{phenyl}N—(C=O)—, {(C$_1$-C$_{20}$)alkoxy}{phenyl}N—(C=O)—, {(C$_3$-C$_{25}$)heteroaryl}{phenyl}N—(C=O)—, {(C$_3$-C$_{25}$)heterocyclic}{phenyl}N—(C=O)—, {(C$_2$-C$_{20}$)alkenyl}{phenyl}N—(C=O)—, {(C$_3$-C$_{20}$)cycloalkynyl}{phenyl}N—(C=O)—, {(C$_5$-C$_{25}$)aryl}{phenyl}N—(C=O)—, {perhalo(C$_1$-C$_{20}$)alkyl}{phenyl}N—(C=O)—, NO—(C=O)—, (C$_1$-C$_{20}$)alkyl-(C=O)—, (C$_3$-C$_{25}$)heteroaryl-(C=O)—, (C$_3$-C$_{25}$)heterocyclic-(C=O)—, (C$_2$-C$_{20}$)alkenyl-(C=O)—, (C$_3$-C$_{20}$)cycloalkenyl-(C=O)—, (C$_2$-C$_{20}$)alkynyl-(C=O)—, (C$_5$-C$_{25}$)aryl-(C=O)—, perhalo(C$_1$-C$_{20}$)alkyl-(C=O)—, phenyl—(C=O)—, (C$_1$-C$_{20}$)alkyl-O—(C=O)—, (C$_3$-C$_{25}$)heteroaryl-O—(C=O)—, (C$_3$-C$_{25}$)heterocyclic-O—(C=O)—, (C$_2$-C$_{20}$)alkenyl-O—(C=O)—, (C$_3$-C$_{20}$)cycloalkenyl-O—(C=O)—, (C$_2$-C$_{20}$)alkynyl-O—(C=O)—, (C$_5$-C$_{25}$)aryl-O—(C=O)—, perhalo(C$_1$-C$_{20}$)alkyl-O—(C=O)—, phenyl-O—(C=O)—, (C$_1$-C$_{20}$)alkyl-(C=O)—O—, (C$_3$-C$_{25}$)heteroaryl-(C=O)—O—, (C$_3$-C$_{25}$)heterocyclic-(C=O)—O—, (C$_2$-C$_{20}$)alkenyl-(C=O)—O—, (C$_3$-C$_{20}$)cycloalkenyl-(C=O)—O—, (C$_2$-C$_{20}$)alkynyl-(C=O)—O—, (C$_5$-C$_{25}$)aryl-(C=O)—O—, phenyl-(C=O)—O—, perhalo(C$_1$-C$_{20}$)alkyl-(C=O)—O—, and salts thereof.

and wherein two independently chosen R$^1$ or R$^{1'}$ alkyl-containing groups may be taken together with any atom to which they are attached to form a three to forty membered cyclic, heterocyclic or heteroaryl ring.

In another embodiment, Z has the formula:

wherein Q and T are each independently selected from the group consisting R$^{10}$(CO)NR$^{11}$—, —(CO)NR$^{10}$—, —NR$^{10}$(CO)—, —NR$^{10}$—, salts thereof, —O—, optionally substituted alkylene, optionally substituted arylene, optionally substituted heteroarylene, and combinations thereof;

wherein A, R$^2$, R$^3$, R$^4$, R$^5$, R$^6$, R$^7$, A$^2$, R$^{10}$, and R$^{11}$ are defined herein;

wherein if substituted, the alkylene, arylene, and heteroarylene are each independently substituted with 0 to 4 groups selected from the group consisting of H, halogen, OR, NR$^1$R$^{1'}$, NR$^1$CO, CONR$^1$, COR$^1$, SR$^1$, SO$_2$R$^1$, SO$_2$NR$^1$, SOR$^1$, alkyl, aryl, heteroalkyl, and heteroaryl, salts thereof, and combinations thereof;

and wherein R$^1$ and R$^{4'}$ being each independently selected from the group including alkyl, aryl, heteroalkyl, and heteroaryl.

In one embodiment, each of said alkylene, cycloalkylene or arylene in said Q and/or T may be independently substituted with one or more substituent groups selected from the group consisting of hydroxy, halo, bromo, chloro, iodo, fluoro, —N$_3$, —CN, —NC, —SH, —NO$_2$, —NH$_2$, salts thereof, and combinations thereof.

In another embodiment, each of said alkylene, cycloalkylene or arylene in said Q and/or T may be independently substituted with one or more substituent groups selected from the group consisting of (C$_1$-C$_{20}$)alkyl, phenyl, (C$_3$-C$_{20}$)cycloalkyl, (C$_1$-C$_{20}$)alkoxy, (C$_3$-C$_{25}$)heteroaryl, (C$_3$-C$_{25}$)heterocyclic, (C$_2$-C$_{20}$)alkenyl, (C$_3$-C$_{20}$)cycloalkenyl, (C$_2$-C$_{20}$)alkynyl, (C$_5$-C$_{20}$)cycloalkynyl, (C$_5$-C$_{25}$)aryl, perhalo(C$_1$-C$_{20}$)alkyl, and a combination thereof.

In another embodiment, each of said alkylene, cycloalkylene or arylene in said Q and/or T may be independently substituted with one or more substituent groups selected from the group consisting of independently substituted with one or more substituent groups selected from the group consisting of (C$_1$-C$_{20}$)alkyl-O—, phenyl-O—, (C$_3$-C$_{20}$)cycloalkyl-O—, (C$_3$-C$_{25}$)heteroaryl-S—, (C$_3$-C$_{25}$)heterocyclic-S—, (C$_2$-C$_{20}$)alkenyl-O—, (C$_3$-C$_{20}$)cycloalkenyl-O—, (C$_2$-C$_{20}$)alkynyl-O—, (C$_5$-C$_{20}$)cycloalkynyl-O—, (C$_5$-C$_{25}$)aryl-O—, perhalo(C$_1$-C$_{20}$)alkyl-O—, and a combination thereof.

In another embodiment, each of said alkylene, cycloalkylene or arylene in said Q and/or T may be independently substituted with one or more substituent groups selected from the group consisting of independently substituted with one or more substituent groups selected from the group consisting of (C$_1$-C$_{20}$)alkyl-S—, phenyl-S—, (C$_3$-C$_{20}$)cycloalkyl-S—, (C$_3$-C$_{25}$)heteroaryl-S—, (C$_3$-C$_{25}$)heterocyclic-S—, (C$_2$-C$_{20}$)alkenyl-S—, (C$_3$-C$_{20}$)cycloalkenyl-S—, (C$_2$-C$_{20}$)alkynyl-S—, (C$_5$-C$_{20}$)cycloalkynyl-S—, (C$_5$-C$_{25}$)aryl-S—, perhalo(C$_1$-C$_{20}$)alkyl-S—, and a combination thereof.

In another embodiment, each of said alkylene, cycloalkylene or arylene in said Q and/or T may be independently substituted with one or more substituent groups selected from the group consisting of independently substituted with one or more substituent groups selected from the group consisting of (C$_1$-C$_{20}$)alkyl-SO$_2$—, phenyl-SO$_2$—, (C$_3$-C$_{20}$)cycloalkyl-SO$_2$, (C$_1$-C$_{20}$)alkoxy-SO$_2$, (C$_3$-C$_{25}$)heteroaryl-SO$_2$—, (C$_3$-

$C_{25}$)heterocyclic-$SO_2$—, ($C_2$-$C_{20}$)alkenyl-$SO_2$—, ($C_3$-$C_{20}$)cycloalkenyl-$SO_2$—, ($C_2$-$C_{20}$)alkynyl-$SO_2$—, ($C_5$-$C_{20}$)cycloalkynyl-$SO_2$—, ($C_5$-$C_{25}$)aryl-$SO_2$—, perhalo($C_1$-$C_{20}$)alkyl-$SO_2$—, and a combination thereof.

In another embodiment, each of said alkylene, cycloalkylene or arylene in said Q and/or T may be independently substituted with one or more substituent groups selected from the group consisting of independently substituted with one or more substituent groups selected from the group consisting of $H_2N$—$SO_2$, ($C_1$-$C_{20}$)alkyl-NH—$SO_2$—, phenyl-NH—$SO_2$—, ($C_3$-$C_{20}$)cycloalkyl-NH—$SO_2$, ($C_1$-$C_{20}$)alkoxy-NH—$SO_2$—, ($C_3$-$C_{25}$)heteroaryl-NH—$SO_2$—, ($C_3$-$C_{25}$)heterocyclic-NH—$SO_2$—, ($C_2$-$C_{20}$)alkenyl-NH—$SO_2$—, ($C_3$-$C_{20}$)cycloalkenyl-NH—$SO_2$—, ($C_2$-$C_{20}$)alkynyl-NH—$SO_2$—, ($C_5$-$C_{20}$)cycloalkynyl-NH—$SO_2$—, ($C_5$-$C_{25}$)aryl-NH—$SO_2$—, perhalo($C_1$-$C_{20}$)alkyl-NH—$SO_2$—, salts thereof, and a combination thereof.

In another embodiment, each of said alkylene, cycloalkylene or arylene in said Q and/or T may be independently substituted with one or more substituent groups selected from the group consisting of independently substituted with one or more substituent groups selected from the group consisting of {($C_1$-$C_{20}$)alkyl}$_2$N—$SO_2$—, {phenyl}$_2$N—$SO_2$—, {($C_3$-$C_{20}$)cycloalkyl}$_2$N—$SO_2$, {($C_1$-$C_{20}$)alkoxy}$_2$N—$SO_2$—, {($C_3$-$C_{25}$)heteroaryl}$_2$N—$SO_2$—, {($C_3$-$C_{25}$)heterocyclic}$_2$N—$SO_2$—, {($C_2$-$C_{20}$)alkenyl}$_2$N—$SO_2$—, {($C_2$-$C_{20}$)alkynyl}$_2$N—$SO_2$—, {($C_5$-$C_{20}$)cycloalkynyl}$_2$N—$SO_2$—, {($C_5$-$C_{25}$)aryl}$_2$N—$SO_2$—, {perhalo($C_1$-$C_{20}$)alkyl}$_2$N—$SO_2$—, salts thereof, and a combination thereof.

In another embodiment, each of said alkylene, cycloalkylene or arylene in said Q and/or T may be independently substituted with one or more substituent groups selected from the group consisting of ($C_1$-$C_{20}$)alkyl-$SO_2$—NH—, phenyl-$SO_2$—NH—, ($C_3$-$C_{20}$)cycloalkyl-$SO_2$—NH—, ($C_1$-$C_{20}$)alkoxy-$SO_2$—NH—, ($C_3$-$C_{25}$)heteroaryl-$SO_2$—NH—, ($C_3$-$C_{25}$)heterocyclic-$SO_2$—NH—, ($C_2$-$C_{20}$)alkenyl-$SO_2$—NH—, ($C_3$-$C_{20}$)cycloalkenyl-$SO_2$—NH—, ($C_2$-$C_{20}$)alkynyl-$SO_2$—NH—, ($C_5$-$C_{20}$)cycloalkynyl-$SO_2$—NH—, ($C_5$-$C_{25}$)aryl-$SO_2$—NH—, perhalo($C_1$-$C_{20}$)alkyl-$SO_2$—NH—, salts thereof, and a combination thereof.

In another embodiment, each of said alkylene, cycloalkylene or arylene in said Q and/or T may be independently substituted with one or more substituent groups selected from the group consisting of ($C_1$-$C_{20}$)alkyl-NH—, phenyl-NH—, ($C_3$-$C_{20}$)cycloalkyl-NH—, ($C_1$-$C_{20}$)alkoxy-NH—, ($C_3$-$C_{25}$)heteroaryl-NH—, ($C_3$-$C_{25}$)heterocyclic-NH—, ($C_2$-$C_{20}$)alkenyl-NH—, ($C_3$-$C_{20}$)cycloalkenyl-NH—, ($C_2$-$C_{20}$)alkynyl-NH—, ($C_5$-$C_{20}$)cycloalkynyl-NH—, ($C_5$-$C_{25}$)aryl-NH—, perhalo($C_1$-$C_{20}$)alkyl-NH—, salts thereof, and a combination thereof.

In another embodiment, each of said alkylene, cycloalkylene or arylene in said Q and/or T may be independently substituted with one or more substituent groups selected from the group consisting of {($C_1$-$C_{20}$)alkyl}$_2$N—, {phenyl}$_2$N—, {($C_3$-$C_{20}$)cycloalkyl}$_2$N—, {($C_1$-$C_{20}$)alkoxy}$_2$N—, {($C_3$-$C_{25}$)heteroaryl}$_2$N—, {($C_3$-$C_{25}$)heterocyclic}$_2$N—, {($C_3$-$C_{20}$)alkenyl}$_2$N, {($C_2$-$C_{20}$)alkynyl}$_2$N—, {($C_5$-$C_{20}$)cycloalkynyl}$_2$N—, {($C_5$-$C_{25}$)aryl}$_2$N—, {perhalo($C_1$-$C_{20}$)alkyl}$_2$N—, salts thereof, and a combination thereof.

In another embodiment, each of said alkylene, cycloalkylene or arylene in said Q and/or T may be independently substituted with one or more substituent groups selected from the group consisting of ($C_1$-$C_{20}$)alkyl-(C=O)—NH—, phenyl-(C=O)—NH—, ($C_3$-$C_{20}$)cycloalkyl-(C=O)—NH—, ($C_1$-$C_{20}$)alkoxy-(C=O)—NH—, ($C_3$-$C_{25}$)heteroaryl-(C=O)—NH—, ($C_3$-$C_{25}$)heterocyclic-(C=O)—NH—, ($C_2$-$C_{20}$)alkenyl-(C=O)—NH—, ($C_3$-$C_{20}$)cycloalkenyl-(C=O)—NH—, ($C_2$-$C_{20}$)alkynyl-(C=O)—NH—, ($C_5$-$C_{20}$)cycloalkynyl-(C=O)—NH—, ($C_5$-$C_{25}$)aryl-(C=O)—NH—, perhalo($C_1$-$C_{20}$)alkyl-(C=O)—NH—, salts thereof, and a combination thereof.

In another embodiment, each of said alkylene, cycloalkylene or arylene in said Q and/or T may be independently substituted with one or more substituent groups selected from the group consisting of ($C_1$-$C_{20}$)alkyl-(C=O)-{(($C_1$-$C_{20}$)alkyl)N}—, phenyl-(C=O)-{(($C_1$-$C_{20}$)alkyl)N}—, ($C_3$-$C_{20}$)cycloalkyl-(C=O)-{(($C_1$-$C_{20}$)alkyl)N}—, ($C_1$-$C_{20}$)alkoxy-(C=O)-{(($C_1$-$C_{20}$)alkyl)N}—, ($C_3$-$C_{25}$)heteroaryl-(C=O)-{(($C_1$-$C_{20}$)alkyl)N}—, ($C_3$-$C_{25}$)heterocyclic-(C=O)-{(($C_1$-$C_{20}$)alkyl)N}—, ($C_2$-$C_{20}$)alkenyl-(C=O)-{(($C_1$-$C_{20}$)alkyl)N}—, ($C_3$-$C_{20}$)cycloalkenyl-(C=O)-{(($C_1$-$C_{20}$)alkyl)N}—, ($C_2$-$C_{20}$)alkynyl-(C=O)-{(($C_1$-$C_{20}$)alkyl)N}—, ($C_5$-$C_{20}$)cycloalkynyl-(C=O)-{(($C_1$-$C_{20}$)alkyl)N}—, ($C_5$-$C_{25}$)aryl-(C=O)-{(($C_1$-$C_{20}$)alkyl)N}—, perhalo($C_1$-$C_{20}$)alkyl-(C=O)-{(($C_1$-$C_{20}$)alkyl)N}—, salts thereof, and a combination thereof.

In another embodiment, each of said alkylene, cycloalkylene or arylene in said Q and/or T may be independently substituted with one or more substituent groups selected from the group consisting of phenyl-(C=O)—NH—, phenyl-(C=O)-{(phenyl)N}—, ($C_1$-$C_{20}$)alkyl-(C=O)-{(phenyl)N}—, ($C_3$-$C_{20}$)cycloalkyl-(C=O)-{(phenyl)N}—, ($C_1$-$C_{20}$)alkoxy-(C=O))-{(phenyl)N}—, ($C_3$-$C_{25}$)heteroaryl-(C=O)-{(phenyl)N}—, ($C_3$-$C_{25}$)heterocyclic-(C=O)-{(phenyl)N}—, ($C_2$-$C_{20}$)alkenyl-(C=O){(phenyl)N}—, ($C_3$-$C_{20}$)cycloalkenyl-(C=O)-{(phenyl)N}—, ($C_2$-$C_{20}$)alkynyl-(C=O)-{(phenyl)N}—, ($C_5$-$C_{20}$)cycloalkynyl-(C=O)-{(phenyl)N}—, ($C_5$-$C_{25}$)aryl-(C=O)-{(phenyl)N}—, perhalo($C_1$-$C_{20}$)alkyl-(C=O)-{(phenyl)N}—, salts thereof, and a combination thereof.

In another embodiment, each of said alkylene, cycloalkylene or arylene in said Q and/or T may be independently substituted with one or more substituent groups selected from the group consisting of $H_2$N(C=O)—, ($C_1$-$C_{20}$)alkyl-NH—(C=O)—, phenyl-NH—(C=O)—, ($C_3$-$C_{20}$)cycloalkyl-NH—(C=O)—, ($C_1$-$C_{20}$)alkoxy-NH—(C=O)—, ($C_3$-$C_{25}$)heteroaryl-MH—(C=O)—, ($C_3$-$C_{25}$)heterocyclic-NH—(C=O)—, ($C_2$-$C_{20}$)alkenyl-NH—(C=O)—, ($C_3$-$C_{20}$)cycloalkenyl-NH—(C=O)—, ($C_2$-$C_{20}$)alkynyl-NH—(C=O)—, ($C_5$-$C_{20}$)cycloalkynyl-NH—(C=O)—, ($C_5$-$C_{25}$)aryl-NH—(C=O)—, perhalo($C_1$-$C_{20}$)alkyl-NH—(C=O)—, salts thereof, and a combination thereof.

In another embodiment, each of said alkylene, cycloalkylene or arylene in said Q and/or T may be independently substituted with one or more substituent groups selected from the group consisting of {($C_1$-$C_{20}$)alkyl}$_2$N—(C=O)—, {phenyl}{($C_1$-$C_{20}$)alkyl}N—(C=O)—, {($C_3$-$C_{20}$)cycloalkyl}{($C_1$-$C_{20}$)alkyl}N—(C=O)—, {($C_1$-$C_{20}$)alkoxy}{($C_1$-$C_{20}$)alkyl}N—(C=O)—, {($C_3$-$C_{25}$)heteroaryl}{($C_1$-$C_{20}$)alkyl}N—(C=O)—, {($C_3$-$C_{25}$)heterocyclic}{($C_1$-$C_{20}$)alkyl}N—(C=O)—, {($C_2$-$C_{20}$)alkenyl}{($C_1$-$C_{20}$)alkyl}N—(C=O)—, {($C_3$-$C_{20}$)cycloalkenyl}{($C_1$-$C_{20}$)alkyl}N—(C=O)—, {($C_2$-$C_{20}$)alkynyl}{($C_1$-$C_{20}$)alkyl}N—(C=O)—, {($C_5$-$C_{20}$)cycloalkynyl}{($C_1$-$C_{20}$)alkyl}N—(C=O)—, {($C_5$-$C_{25}$)aryl}{($C_1$-$C_{20}$)alkyl}N—(C=O)—, {perhalo($C_1$-$C_{20}$)alkyl}{($C_1$-$C_{20}$)alkyl}NH-13 (C=O)—, salts thereof, and a combination thereof.

In another embodiment, each of said alkylene, cycloalkylene or arylene in said Q and/or T may be independently substituted with one or more substituent groups selected from the group consisting of {phenyl}$_2$N—(C=O)—, {($C_3$-$C_{20}$)cycloalkyl}{phenyl}N—(C=O)—, {($C_1$-$C_{20}$)

alkoxy}{phenyl}N—(C=O)—, {($C_3$-$C_{25}$)heteroaryl}{phenyl}N—(C=O)—, {($C_3$-$C_{25}$)heterocyclic}{phenyl}N—(C=O)—, {($C_2$-$C_{20}$)alkenyl}{phenyl}N—(C=O)—, {($C_3$-$C_{20}$)cycloalkenyl}{phenyl}N—(C=O)—, {($C_2$-$C_{20}$)alkynyl}{phenyl}N—(C=O)—, {($C_5$-$C_{20}$)cycloalkynyl}{phenyl}N—(C=O)—, {($C_5$-$C_{25}$)aryl}{phenyl}N—(C=O)—, {perhalo($C_1$-$C_{20}$)alkyl}{phenyl}N—(C=O)—, salts thereof, and a combination thereof.

In another embodiment, each of said alkylene, cycloalkylene or arylene in said Q and/or T may be independently substituted with one or more substituent groups selected from the group consisting of HO—(C=O)—, ($C_1$-$C_{20}$)alkyl-(C=O)—, ($C_3$-$C_{25}$)heteroaryl-(C=O)—, ($C_3$-$C_{25}$)heterocyclic-(C=O)—, ($C_2$-$C_{20}$)alkenyl-(C=O)—, ($C_3$-$C_{20}$)cycloalkenyl-(C=O)—, ($C_2$-$C_{20}$)alkynyl-(C=O)—, ($C_5$-$C_{25}$)aryl-(C=O)—, perhalo($C_1$-$C_{20}$)alkyl-(C=O)—, phenyl-(C=O)—, and a combination thereof.

In another embodiment, each of said alkylene, cycloalkylene or arylene in said Q and/or T may be independently substituted with one or more substituent groups selected from the group consisting of ($C_1$-$C_{20}$)alkyl-O—(C=O)—, ($C_3$-$C_{25}$)heteroaryl-O—(C=O)—, ($C_3$-$C_{25}$)heterocyclic-O—(C=O)—, ($C_2$-$C_{20}$)alkenyl-O—(C=O)—, ($C_3$-$C_{20}$)cycloalkenyl-O—(C=O)—, ($C_2$-$C_{20}$)alkynyl-O—(C=O)—, ($C_5$-$C_{25}$)aryl-O—(C=O)—, perhalo($C_1$-$C_{20}$)alkyl-O—(C=O)—, phenyl-O—(C=O)—, and a combination thereof.

In another embodiment, each of said alkylene, cycloalkylene or arylene in said Q and/or T may be independently substituted with one or more substituent groups selected from the group consisting of ($C_1$-$C_{20}$)alkyl-(C=O)—O—, ($C_3$-$C_{25}$)heteroaryl-(C=O)—O—, ($C_3$-$C_{25}$)heterocyclic-(C=O)—O—, ($C_2$-$C_{20}$)alkenyl-(C=O)—O—, ($C_3$-$C_{20}$)cycloalkenyl-(C=O)—O—, ($C_2$-$C_{20}$)alkynyl-(C=O)—O—, ($C_5$-$C_{25}$)aryl-(C=O)—O—, phenyl-(C=O)—O—, perhalo($C_1$-$C_{20}$)alkyl-(C=O)—O—, and a combination thereof.

When the Z group or any of its constituent A, Q, T, or CRR groups are substituted, the substituent is preferably a pharmaceutically acceptable or suitable substituent. This type of substituent is intended to mean a chemically and pharmaceutically acceptable functional group (e.g., a moiety that does not negate the desired activity of the active compound.)

In one embodiment, suitable pharmaceutically acceptable substituents include, but are not limited to halo groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO-(C=O)— groups, amino groups, alkyl- and dialkylamino groups, carbamoyl groups, alkylcarbonyl groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups and the like.

As used herein, the term, "alkylene" refers to a diradical alkane species that contains 1, 2, 3, 4, 5, 6, 7, 8, 9, 10, 11, 12, 13, 14, 15, 16, 17, 18, 19 and 20 carbons or any subrange of carbons therebetween. The alkylene may be branched or unbranched, saturated or unsaturated, and substituted or unsubstituted. In addition, any carbon atom therein may be optionally replaced with one or more heteroatoms such as nitrogen, oxygen or sulfur or any combination thereof.

As used herein, the term, "cycloalkylene" refers to a diradical cycloalkane species that contains 3, 4, 5, 6, 7, 8, 9, 10, 11, 12, 13, 14, 15, 16, 17, 18, 19 and 20 ring carbons or any subrange of carbons therebetween. The cycloalkylene may be branched or unbranched, saturated or unsaturated, and substituted or unsubstituted. In addition, any carbon atom therein may be optionally replaced with one or more heteroatom such as nitrogen, oxygen or sulfur or any combination thereof.

As used herein, the term "arylene" means an aromatic diradical species having 5, 6, 7, 8, 9, 10, 11, 12, 13, 14, 15, 16, 17, 18, 19, 20, 21, 22, 23, 24 and 25 carbons and any subrange of carbons thereof. These may be unsubstituted or substituted as indicated herein. In addition, any carbon atom therein may be optionally replaced with one or more heteroatom such as nitrogen, oxygen or sulfur or any combination thereof to form a heteroarylene.

As used herein, the term "alkyl" as well as the alkyl moieties of or within other groups referred to herein (e.g., ($C_1$-$C_{20}$)alkyl, ($C_1$-$C_{20}$)alkoxy, ($C_2$-$C_{20}$)alkenyl, ($C_2$-$C_{20}$)alkynyl, and perhalo($C_1$-$C_{20}$)alkyl) include alkyl moieties having 1, 2, 3, 4, 5, 6, 7, 8, 9, 10, 11, 12, 13, 14, 15, 16, 17, 18, 19 and 20 carbons or any subrange of carbons therebetween. They may be linear or branched (such as methyl, ethyl, n-propyl, isopropyl, n-butyl, iso-butyl, secondary-butyl, tertiary-butyl, etc.). They may be saturated or unsaturated as indicated by the "alkenyl" or "alkynyl" terminology. Other than the perhaloalkyl, which are completely substituted by one or more of the same or different halogens, the alkyl groups may be unsubstituted or substituted as indicated herein.

As used herein, the term "cycloalkyl" as well as the other moieties having cyclic groups referred to herein (for example ($C_3$-$C_{20}$)cycloalkyl, ($C_3$-$C_{20}$)cycloalkenyl and ($C_5$-$C_{20}$)cycloalkynyl) refers to mono carbocyclic moieties having 3, 4, 5, 6, 7, 8, 9, 10, 11, 12, 13, 14, 15, 16, 17, 18, 19 and 20 ring carbons or any subrange of carbons therebetween. They may be unsubstituted or substituted as indicated herein.

As used herein, the terms, "alkenyl," "alkynyl," "cycloalkynyl," and "cycloalkenyl" refer to unsaturated radical species having 1, 2, 3, 4, 5, 6, 7, 8, 9, 10, 11, 12, 13, 14, 15, 16, 17, 18, 19 and 20 carbons (or, for the cyclic species 3, 4, 5, 6, 7, 8, 9, 10, 11, 12, 13, 14, 15, 16, 17, 18, 19 and 20 ring carbons) or any subrange of carbons or ring carbons therebetween. They may be branched or unbranched, and they may be unsubstituted or substituted as indicated herein. These groups have one or more than one site of unsaturation, i.e., one or more double or triple bonds. For example, these moieties may have one, two, three, four or more sites of unsaturation. Some unlimiting examples of these include ethenyl, 1-propenyl, 2-propenyl (allyl), iso-propenyl, 2-methyl-1-propenyl, 1-butenyl, 2-butenyl, ethynyl, 1-propynyl, 2-propynyl, 1-butynyl, and 2-butynyl.

As used herein, the term, "alkoxy" refers to alkylQ radical species having 1, 2, 3, 4, 5, 6, 7, 8, 9, 10, 11, 12, 13, 14, 15, 16, 17, 18, 19 and 20 carbons or any subrange of carbons therebetween. They may be unsubstituted or substituted as indicated herein.

As used herein, the term "halogen" or "halo" includes fluoro, chloro, bromo or iodo, and any combinations thereof.

As used herein, the term "aryl" means aromatic radicals having 5, 6, 7, 8, 9, 10, 11, 12, 13, 14, 15, 16, 17, 18, 19, 20, 21, 22, 23, 24 and 25 carbons and any subrange of carbons thereof. These may be unsubstituted or substituted as indicated herein. Nonlimiting examples include phenyl, naphthyl, tetrahydronaphthyl, indanyl and the like.

As used herein, the term "heteroaryl" refers to an aromatic heterocyclic group with at least one heteroatom selected from O, S and N in the ring and having 3, 4, 5, 6, 7, 8, 9, 10, 11, 12, 13, 14, 15, 16, 17, 18, 19, 20, 21, 22, 23, 24 and 25 ring carbons and any subrange of carbons thereof. The heteroatoms may be present either alone or in any combination. The heteroaryl groups may be unsubstituted or substituted as indicated herein. One, two, three, four or more heteroatoms may be present. In addition to said heteroatom, the aromatic group may optionally have up to four N atoms in the ring. Nonlimiting examples of heteroaryl groups include pyridyl, pyrazinyl, pyrimidinyl, pyridazinyl, thienyl, furyl, imidzaolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, and the like; which are optionally unsubstituted or substituted with one or more substituent groups as indicated herein.

The term "heterocyclic" as used herein refers to a cyclic group containing 3, 4, 5, 6, 7, 8, 9, 10, 11, 12, 13, 14, 15, 16, 17, 18, 19, 20, 21, 22, 23, 24 and 25 ring carbons and any subrange of carbons thereof carbon atoms and hetero atoms selected from N, O, S or NR'. Nonlimiting examples include azetidinyl tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, indolinyl, isoindolinyl, quinuclidinyl, chromanyl, isochromanyl, benzoxazinyl and the like. Examples of such monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, 1,4-oxazin-2-yl, 1,2,5-oxathiazin-4-yl and the like; which may be unsubstituted or optionally substituted with one or more substituents as indicated herein.

In another embodiment, any of the guanylhydrazone-containing compounds of this invention, with or without additional active agents, may be formulated into therapeutic compositions as natural or salt forms.

According to one embodiment, a guanylhydrazone salt according to the invention includes one or more guanylhydrazone compounds combined with a carboxylic acid. One suitable carboxylic acid for the salt combination includes a chemical structure having one of the following formulas (I and II):

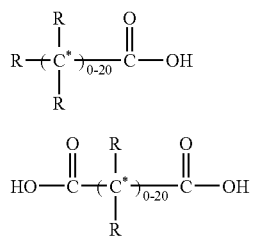

In the carboxylic acid formulas I and II above, C* represents a potentially chiral carbon that can be in either the D or L enantiomeric configuration, and R represents a suitable substituent such as, but not limited to, hydrogen (H), or methyl ($CH_3$) or other alkyl. The "0-20" range includes all values and subranges therebetween, including 0, 1, 2, 3, 4, 5, 6, 7, 9, 10, 11, 12, 13, 14, 15, 16, 17, 18, 19 and 20.

In the carboxylic acid formulas I and II above, a "suitable substituent" is intended to mean a functional group that does not negate the intended activity of the active guanylhydrazone compound in the salt. Nonlimiting examples of suitable substituents include halo groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—(C═O)— groups, amino groups, alkyl- and dialkylamino groups, carbamoyl groups, alkylcarbonyl groups, alkoxycarbonyl groups, alkylaminocarbonyl groups, alkylsulfonyl groups, arylsulfonyl groups and the like. Mixtures are possible.

More particularly, in the carboxylic acid formulas I and II above, each R may be independently selected from Y—, Y—O—, Y—S—, Y—$SO_2$—, $(Y)_2$-N—$SO_2$—, Y—(C═O)—, Y—(C═O)(—, Y—O—(C═O)—, $(Y)_2$—N—, Y—(C═O)—(Y—N)—, (Y—(C═))$_2$—N—, Y—($SO_2$)Y—N)—, or (Y—($SO_2$))$_2$—N—; wherein two independently chosen Y alkyl-containing groups may be taken together with any nitrogen atom to which they are attached to form a three to twelve membered cyclic, heterocyclic or heteroaryl ring, and each Y is independently selected from hydrogen, carboxyl, halo, hydroxyl, thio, nitro, amine, NC—, ($C_1$-$C_6$)alkyl, ($C_3$-$C_6$)cycloalkyl, ($C_2$-$C_6$)alkenyl, ($C_3$-$C_6$)cycloalkenyl, ($C_2$-$C_6$)alkynyl, ($C_3$-$C_6$)cycloalkynyl, ($C_1$-$C_6$)alkoxy, ($C_5$-$C_7$)aryl, ($C_3$-$C_5$)heteroaryl, and ($C_3$-$C_5$) heterocyclic, wherein each of the aforesaid ($C_1$-$C_6$alkyl, ($C_3$-$C_6$)cycloalkyl, ($C_2$-$C_6$)alkenyl, ($C_3$-$C_6$) cycloalkenyl, ($C_2$-$C_6$)alkynyl, ($C_3$-$C_6$)cycloalkynyl, ($C_1$-$C_6$)alkoxy, ($C_5$-$C_7$) aryl, ($C_3$-$C_5$)heteroaryl, and ($C_3$-$C_5$)heterocyclic substituents may be optionally and independently selected from the group consisting of carboxyl, halo, hydroxyl, thiol, nitro, amine, NC—, ($C_1$-$C_4$)alkyl, ($C_1$-$C_4$)alkoxy, ($C_2$-$C_4$)alkenyl, and ($C_2$-$C_4$)alkynyl.

According to another embodiment, the carboxylic acid in the guanylhydrazone salt is described by the following general formula (III):

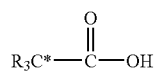

wherein C* and R, independently, are defined as described for the carboxylic acid formulas I and II above. In one aspect of this embodiment the carboxylic acid is acetic acid.

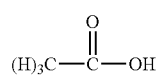

Acetic Acid

According to another embodiment, the carboxylic acid in the guanylhydrazone salt according to the invention is described by the following general formula (IV):

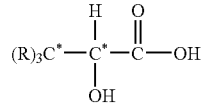

wherein C* and R are defined as described for the carboxylic acid formulas I and II above. In one aspect of this embodiment the carboxylic acid is L-lactic acid:

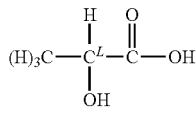

L-Lactic Acid

According to another embodiment, the carboxylic acid in the guanylhydrazone salt according to the invention is described by the following general formula (V):

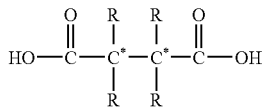

V wherein C* and R are defined as described for the carboxylic acid formulas I and II above. In one aspect of this embodiment the carboxylic acid is L-Aspartic Acid:

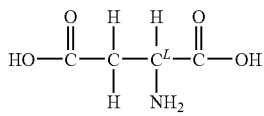

L-Aspartic Acid

According to another embodiment, the carboxylic acid in the guanylhydrazone salt according to the invention is described by the following general formula (IV):

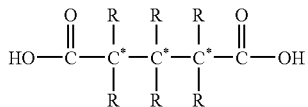

VI wherein C* and R are defined as described for the carboxylic acid formulas I and II above. In one aspect of this embodiment the carboxylic acid is L-glutamic acid:

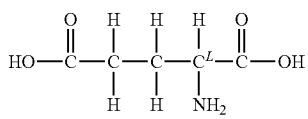

L-Glutamic Acid

According to another embodiment, the guanylhydrazone-carboxylic acid salts according to the invention include a guanylhydrazone compound combined with a carboxylic acid wherein a suitable carboxylic acid for the salt combination, according to this embodiment, is a chemical structure described by the following general formula (VII):

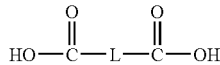

VII wherein L is a diradical moiety selected from a $(C_1-C_{20})$alkyl, $(C_3-C_{20})$cycloalkyl, $(C_2-C_{20})$alkenyl, $(C_3-C_{20})$cycloalkenyl, $(C_2-C_{20})$alkynyl, $(C_3-C_{20})$cycloalkynyl, $(C_1-C_{20})$alkoxy/thiol, $(C_3-C_{20})$aryl, $(C_3-C_{15})$heteroaryl, $(C_3-C_{15})$heterocyclic and $(C_3-C_{20})$cycloalkyl; wherein each of the aforesaid $(C_1-C_{20})$alkyl, $(C_3-C_{20})$cycloalkyl, $(C_2-C_{20})$alkenyl, $(C_3-C_{20})$cycloalkenyl, $(C_2-C_{20})$alkynyl, $(C_3-C_{20})$cycloalkynyl, $(C_1-C_{20})$alkoxy/thiol, $(C_3-C_{20})$aryl, $(C_3-C_{15})$heteroaryl, $(C_3-C_{15})$heterocyclic and $(C_3-C_{20})$cycloalkyl diradical moieties may optionally be substituted, for example, with a halo-substituted alkyl, by one to twenty moieties independently selected from the group consisting carboxyl, halo, hydroxyl, thiol, nitro, amine, Y or R wherein these terms are defined herein.

According to another embodiment, the anion or acid for the guanylhydrazone salt is described by the following general formulas:

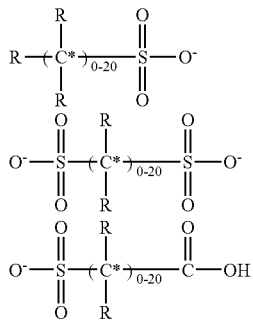

wherein C* and R represent suitable substituents as defined in the formulas I and II above.

According to another embodiment, the anion or acid in the guanylhydrazone salt according to the invention is described by the following general formula:

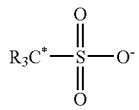

In one aspect of this embodiment, the anion is mesylate.

One embodiment includes a salt wherein a guanylhydrazone compound is combined with L-lactic acid. In another embodiment, the salt is guanylhydrazone compound containing multiple guanylhydrazone moieties and combined with L-lactic acid. In another embodiment, the invention relates to a salt combining the semapimod compound with L-lactic acid.

Other suitable salts include acid addition salts of a guanylhydrazone compound, and in particular semapimod. Suitable acids which are used to prepare the acid addition salts of the guanylhydrazone compounds invention are those which form non-toxic acid addition salts, i.e., salts containing pharmacologically acceptable anions, such as the bromide, iodide, nitrate, sulfate, bisulfate, phosphate, acid phosphate, citrate, acid citrate, tartrate, bitartrate, succinate, fumarate, isosylate, mesylate, gluconate, saccharate, benzoate, methanesulfonae, ethanesulfonate, benzenesulfonate, p-toluenesulfonate and pamoate (i.e., 1,1'methylene-bis-(2-hydroxy-3-naphthoate)) salts.

Other salts can also be made using a guanylhydrazone, such as semapimod and benzensulfonate, benzoate, bicarbonate, bitartrate, edetate, camyslate, carbonate, citrate, dihydrochloride, edentate, edisylate, estolate, esylate, fumarate, gluceptate, glucoheptonate, gluconate, glutamate, glycollylarsanilate, hexylresorcinate, hydrabamine, hydrobromide, hydrochloride, hydroxynaphthoate, chloride, bromide, iodide, isethionate, lactate, lactobionate, malate, mandelate, mesylate, methylbromide, methylnitrate, methylsulfate, mucate, napsylate, nitrate, pamoate, pantothenate, phosphate or diphosphate, polygalacturante, salicylate, stearate, subacetate, succinate, sulfate, tannate, teoclate, and triethiodide salts.

Other suitable salts include sodium, potassium, ammonium, calcium, or ferric hydroxide salts, and isopropylamine, trimethylamine, 2-ethylamino ethanol, histidine, procaine, hydrochloric or phosphoric acids, organic acids such as acetic, oxalic, tartaric, mandelic, and the like.

Any ratio of guanylhydrazone:counterion in the salt form, for example, guanylhydrazone:counterion ratios of 10, 9, 8, 7, 6, 5, 4, 3, 2, 1:1, 2, 3, 4, 5, 6, 7, 8, 9, 10 is suitable. The ratio can be expressed as the number of "Ghy" groups:counterions or as the number of ionic guanylhydrazone molecules:counterions as appropriate. In one embodiment, either the guanylhydrazone or the counterion or both may be multivalent, and the ratio is adjusted accordingly such that the salt may adopt a zero or non-zero charge. Mixed salts are possible.

The term "treating" as used herein includes inhibition or prophylaxis of the named condition or amelioration or elimination of the condition once it has been established. As noted above, the guanylhydrazone compounds described herein are useful for agricultural or veterinary health purposes as well as for the treatment of a human patient.

As used herein, the term "therapeutically effective amount" refers to an amount of the compound or salt or a combination of compounds or salts which is effective, upon single or multiple dose administration or continuous administration, infusion or application to the patient, for the inhibition, treatment, and/or prevention of NEC, a condition associated with the release of HMGB1, a condition associated with the release of iNOS protein, a condition associated with the release of Bax protein, a condition associated with the release of Bad protein, a condition associated with the release of COX-2 protein, or a condition associated with the release of RAGE, or a combination thereof, and/or maladies associated with low-birth weight, formula feeding, bacterial colonization of the gut, or hypoxia, or a combination thereof, and/or to reduce or downregulate the release or expression of HMGB1, to reduce or downregulate the release or expression of iNOS protein, to reduce or downregulate the release or expression of Bax protein, to reduce or downregulate the release or expression of Bad protein, to reduce or downregulate the release or expression of COX-2 protein, or to reduce or downregulate the release or expression of RAGE, or a combination thereof, for example. The term "therapeutically effective amount" also refers to an amount of a guanylhydrazone compound which is effective in providing inhibitor or preventive activity in a patient in need thereof or reasonably expected to be in need thereof. As used herein the term "inhibiting" does not necessarily refer to a total elimination of the malady or condition.

A therapeutically effective amount can be readily determined by the attending diagnostician, as one skilled in the art, by the use of known techniques nad by observing results obtained under analogous circumstances. In determining the therapeutically effective amount or dose, a number of factors are considered by the attending diagnostician, including, but not limited to: the species of mammal; its size, age, and general health; the specific disease involved; the degree of or involvement or the severity of the disease; the response of the individual mammal; the particular compound administered; the bioavailability characteristics of the preparation administered; the dose regimen selected; the use of concomitant medication; and other relevant circumstances.

A therapeutically effective amount of the guanylhydrazone-containing compound may range from about 0.0001 milligram per kilogram of body weight per day (mg/kg/day) to about 10,000 mg/kg/day. Preferred amounts may range from about 0.0001 to about 100 mg/kg/day. These ranges include all values and subranges therebetween, including 0.0001, 0.0005, 0.001, 0.005, 0.01, 0.05, 0.1, 0.5, 1, 1, 2, 3, 4, 5, 6, 7, 8, 9, 10, 100, 1,000, 5,000, and 10,000 mg/kg/day, and any combination thereof.

The guanylhydrazone compound according to the invention can be administered to the mammal in any form or mode which makes the compound bioavailable in effective amounts, including oral and parental routes. For example, semapimod can be administered orally, intracerebroventricularly, subcutaneously intramuscularly, intravenously, transdermally, intranasally, rectally, topically, intramucosaly, intravaginally, parenteraly, and the like. Oral, topical, intravenous or intramuscular administration is generally preferred. One skilled in the art of preparing formulations can readily select the proper form and mode of administration depending upon the particular characteristics of the compound selected, the disease state to be treated, the stage of the disease, and other relevant circumstances.

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered, where appropriate, in the form of their pharmaceutically acceptable acid addition salts for purposes of stability, convenience of crystallization, increased solubility and the like These compounds and compositions can be administered to mammals for veterinary use. For example, domestic animals can be treated in much the same way as a human clinical patient. In general, the dosage required for therapeutic effect will vary according to the type of use, mode of administration, as well as the particularized requirements of the individual hosts. Typically, dosages will range from about 0.0001 to 10,000 mg/kg, and more usually 0.001 to 100 mg/kg of the host body weight. These ranges include all values and subranges therebetween, including 0.0001, 0.0005, 0.001, 0.005, 0.01, 0.05, 0.1, 0.5, 1, 2, 3, 4, 5, 6, 7, 8, 9, 10, 100, 1,000, 5,000, and 10,000 mg/kg, and any combination thereof.

Alternatively, dosages within these ranges can be administered by constant infusion over an extended period of time, for example, exceeding 24 hours, until the desired therapeutic, preventive, and/or inhibiting benefits are obtained. Indeed, drug dosage, as well as route of administration, should be selected on the basis of relative effectiveness, relative toxicity, microbial infection size, presence of other infections, and effect of the guanylhydrazone compound on cell cycle, drug pharmacokinetics, age, sex, physical condition of the patient and prior treatment.

The suitability of particular carriers for inclusion in a given therapeutic composition depends on the preferred route of administration. For example, compositions may be formulated for oral administration. Such compositions are typically prepared as liquid solution or suspensions or in solid forms. Oral formulations usually include such additives as binders, fillers, carriers, preservatives, stabilizing agents, emulsifiers, buffers, mannitol, lactose, starch, magnesium stearate, sodium saccharin, cellulose, magnesium carbonate, and the like. These compositions may take the form of solutions, suspensions, tablets, pills, capsules, sustained release formulations, or powders, and typically contain 1% to 95% by weight of active ingredient. More preferably, the composition contains from about 2% to about 70% active ingredient. These ranges include all values and subranges therebetween, including 1, 2, 3, 4, 5, 6, 7, 8, 9, 10, 20, 30, 40, 50, 60, 70, 80, 90, and 95%, and any combination thereof.

Suitable compositions may be prepared as injectables, either as liquid solutions, suspensions, or emulsions; solid forms suitable for solution in or suspension in liquid prior to injection. Such injectables may be administered subcutaneously, intravenously, intraperitoneally, intramuscularly, intrathecally, or intrapleurally. The active ingredient or ingredients are often mixed with diluents, carriers, or excipients which are physiologically tolerable and compatible with the active ingredient(s). Suitable diluents and excipients are for example, water, saline, dextrose, glycerol, or the like and combinations thereof. In addition, if desired, the compositions may contain minor amounts of auxiliary substances such as wetting or emulsifying agents, stabilizing or pH buffering agents.

Semapimod is a known compound. As for the other guanylhydrazone compounds and salt molecules described herein, suitable methods for obtaining them may be found in U.S. Provisional Application Ser. Nos. 60/601,992, filed Aug. 17, 2004, and 60/582,532, filed Jun. 25, 2004, incorporated herein by reference.

EXAMPLES

Materials and Methods

Reagents

LPS from *Escherichia coli* 0127:B8 was from Sigma (St. Louis, Mo.). Peroxynitrite was from Alexis Biochemicals, San Diego, Calif. The drug semapimod was kindly provided by Cytokine PharmaSciences, Inc., King of Prussia, Pa. The different antibodies used for Western blotting were purchased from the following sources: the rabbit polyclonal anti-Bad (sc943) and anti-Bax (P-19) were from Santa Cruz Biotechnology, Inc. (Santa Cruz, Calif.), the COX-2 (murine) polyclonal antibody was from Cayman Chemical (Ann Arbor, Mich.), the anti-HMGB1 was a polyclonal rabbit antisera against native calf thymus HMG1/HMGB1 from Upstate Biotechnology (Lake Placid, N.Y.), the rabbit polyclonal anti-iNOS antibody was from BD Transduction Laboratories (Lexington, Ky.), the rabbit polyclonal anti-RAGE was from Affinity BioReagents (Golden, Colo.), and the anti-p38 and anti-phospho-p38 were from Cell Signaling Technology (Beverly, Mass.).

Animal Model of NEC

All the experiments were carried out according to an animal protocol approved by the Animal Research and Care Committee (ARCC) of the Children's Hospital of Pittsburgh. Pregnant time-dated Sprague-Dawley rats (Charles River Labs, Wilmington, Mass.) were induced at term using a subcutaneous injection (1 to 2 U per animal) of Pitocin® (Monarch Pharmaceuticals, Bristol, Tenn.). Immediately after birth, the neonates were weighed and randomized into one of the different treatment groups. Group 1 consisted of neonatal rats left with their mother, and thus were breast-fed. Group 2 consisted of neonates separated from their mothers, housed in a temperature and humidity controlled incubator (Ohio Medical Products, Madison, Wis.) and gavaged with a special rodent formula (0.2 ml, see below), two times per day and subjected to 10 min. of hypoxia (5% $O_2$, 95% $N_2$) (Prax Air, Pittsburgh, Pa.) three daily in a modular Chamber (Billups-Rothenberg Inc, Del Mar, Calif.) as follows: pups were fed in the morning post-hypoxia, exposed to a $2^{nd}$ hypoxic insult after 4 hrs, and then subjected to the final hypoxic insult followed by the final feed. Rats in Group 3 were treated in a similar fashion to those in Group 2; however the animals received the experimental drug semapimod (0.1-1 mg/kg, i.p., once daily, vehicle: 5% dextrose) right before hypoxia. The formula composition consists of 15 g Similac 60/40 (Ross Pediatrics, Columbus, Ohio) in 75 ml of Esbilac canine milk replacer (Peg-Ag Inc., Hampshire, Ill.) as described by Barlow et al. (5), and was designed to approximate the protein and caloric content of rat breast milk. The rats were sacrificed on different days as indicated and the intestinal samples (segments of terminal ileum for the present study) were harvested for morphological studies and Western blotting as described below.

Morphologic Evaluation of Intestinal Samples

Rats were sacrificed on different days as indicated and the distal ileum was harvested for morphological studies. For light microscopy, hematoxylin and eosin slides were prepared per standard protocol (15). A pathologist from Children's Hospital of Pittsburgh (Dr. R. Jaffe) blinded to the experimental groups graded the morphological changes in the intestinal epithelium. The criteria for each histological guide (0-3) were as follows: (0) normal: no pathologic change, different epithelial patterns are noted: clear, vacuolar and inclusion-type; (1) mild: occasional neutrophils, separation of villus core and mild damage to enterocytes; (2) moderate: submucosal edema, epithelial sloughing and marked presence of neutrophils; and (3) severe: denudation of epithelium with loss of villi and transmural necrosis or perforation (32).

Western Blotting

Newborn rats were sacrificed as indicated and segments of the terminal ileum were isolated. The mucosa was gently scraped from each segment and immediately placed in cold lysis buffer containing 62.5 mM Tris (pH 6.6), 10% glycerol, 1% sodium dodecyl sulfate (SDS), and protease inhibitors (10 µg/ml leupeptin, 5 µg/ml pepstatin, 2 µg/ml aprotinin, and 0.5 mM phenylmethylsulfonyl fluoride (PMSF), all from Sigma, St. Louis, Mo.). The samples were then homogenized and boiled for 1 min. followed by centrifugation at 10,000×g for 30 min. in order to remove the cell debris. Protein concentration in the supernatant was determined using the bicinchoninic acid (BCA) Protein Assay kit form Sigma (St. Louis, Mo.) with bovine serum albumin as standard. Protein samples (equivalent to 50 µg) were resolved on 12% SDS-polyacrylamide gels using a BioRad mini-gel system (Hercules, Calif.) and then electroblotted onto PVDF membranes (millipore, Bedford, Mass.). After blocking for 1 hr with milk (5% in PBS with 0.1% Tween-20) at room temperature, the membranes were probed for 1 hr at room temperature with the primary antibodies dissolved in 1% milk PBS/Tween at the following dilutions: HMGB1 (1:1000), Bad (1:1000), Bax (1:500), iNOS (1:750), COX-2 (1:500) and RAGE (1:1000). The membranes were then thoroughly washed and incubated with the secondary antibody (horseradish peroxidase-conjugated goat anti-rabbit or goat anti-mouse IgG, Pierce, Rockford, Ill.) at 1:15,000 dilution (in PBS/Tween with 1% milk) for 1 hr prior to detection. Protein bands were visualized using a SuperSignal™ chemiluminescence substrate (Pierce, Rockford, Ill.) according to the manufacturer's instructions.

Cell Culture and Western Blotting

The rat intestinal crypt cell line IEC-6 was purchased from the American Type Culture Collection (ATCC, Manassas, Va.). Cells were grown in tissue culture medium consisting of Dulbeco's modified Eagle's medium with 4.5 gm/L glucose (Bio-Whittaker, Walkersville, Md.) supplemented with 5% fetal bovine serum (Bio-Whittaker), 0.02 mM glutamine (GIBCO; Grand Island, N.Y.), 0.1 U/ml insulin, 100 U/ml penicillin, and 100 μg/ml streptomycin (GIBCO) at 37° C. and 10% $CO_2$. Cells were pretreated with semapimod (0.1-10 μM solutions prepared in 5% dextrose) followed by short exposure to LPS (5 μg/ml), peroxynitrite ($ONOO^-$, 50 μM) or cytomix (a combination of tumor necrosis factor (TNFα, 10 ng/ml), interleukin-1β (IL-β, 1 ng/ml), and interferon-gamma (IFNγ, 1000 U/ml) for 10 min. Preparation of the $ONOO^-$ solution and cell treatment was as previously reported (36). The lysates were collected for Western blotting analysis as follows: proteins were extracted for 10 min at 4° C. witih lysis buffer (20 mM Tris pH 8.0, 150 mM NaCl, 1% NP-40, 0.5% sodium deoxycholate, 0.1% sodium dodecyl-sulfate) supplemented with protease and phosphatase inhibitors: 1 mM PMSF, 1 mM benzamidine, 50 μg/ml aprotinin, 0.5 mM $Na_3VO_4$, 20 mM NaF, and 0.5 mM phenylarsine oxide. Aliquots containing 50 μg total protein were resolved by SDS-polyacrylamide gel electrophoresis. Gels were electroblotted onto nitrocellulose membranes. Following 1 hr incubation in blocking solution (phosphate-buffered saline, 0.1% Tween-20, 2% fish gelatin, pH 7.5), membranes were incubated with primary (phospho-p38 and p38) and secondary horseradish peroxidase-conjugated antibodies as recommended by manufacturers. Membranes were then impregnated with luminol reagent and exposed to x-ray film.

Statistical Analysis

Results are expressed as mean ±SEM or SD as indicated. Differences among groups were analyzed by the Student's t-test, Chi-square test or one-way analysis of variance (ANOVA) followed by Tukey Test or Fisher's Least Significance Difference (LSD) Test where appropriate (SigmaStat™ 2.03; SPSS, Chicago, Ill.).

Results

As shown in FIG. 1, HMGB1 is elevated in formula-fed animals exposed to hypoxia. Newborn rats were randomized into two groups: breast-fed (BF) animals were left with their mothers and formula-fed pups were exposed to hypoxia (FFH) as described in Methods. The terminal ileum of each rat was harvested on day 4 and the mucosal scrapings were processed for protein isolation followed by Western blotting. A representative blot with 3 animals/group and denistometric analysis for HMGB1 protein (30 kDa band) and low molecular weight products (7-10 kDa bands) performed as described. Results in graph bars are the mean±S.E.M. (n=13 animals for each group, *P<0.05 vs. BF control, analyzed by one-way ANOVA followed by Fisher's LSD Test).

Figure 2:
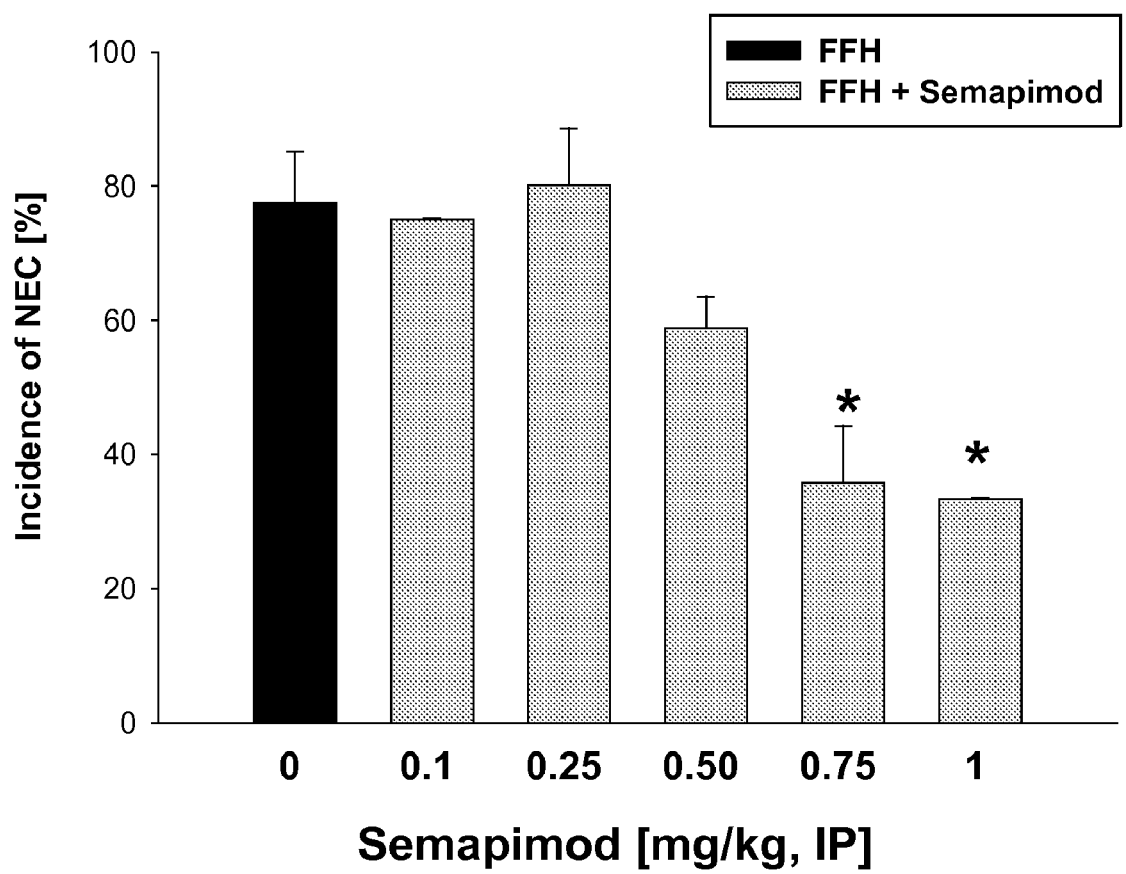
FIG. 2 shows that administration of semapimod in vivo is protective in an experimental NEC model.

As shown in FIG. 2, the administration of semapimod in vivo is protective in an experimental NEC model. Newborn rats separated from their mothers were fed a conventional formula and exposed to hypoxia after administration of the drug semapimod (0.1-1 mg/kg, i.p.) as described in Methods. A segment of the terminal ileum of each rat was harvested on day 4 for morphological analysis as described. Incidence of NEC was calculated as the percentage of animals displaying pathology scores higher than 0 as assessed by histology. Results in graph bars are the mean±S.E.M. (n=15-45 animals for each group, *P<0.05 vs. FFH without semapimod, analyzed by one-way ANOVA followed by Fisher's LSD Test).

As shown in FIG. 3, the administration of semapimod in vivo decreases the expression of HMGB1 and its receptor RAGE in ileal samples from formula-fed animals exposed to hypoxia. Newborn rats were randomized into two groups: breast-fed (BF) animals were left with their mothers, formula-fed pups were exposed to hypoxia without (FFH) or with semapimod (FFH+semapimod) as described in Methods. The terminal ileum of each rat was harvested on day 4 and the mucosal scrapings were processed for protein isolation followed by Western blotting. (a) A representative blot with 3 animals/group and densitometric analysis for HMGB1 protein (30 kDa band). Results in graph bars are the mean±S.E.M. (n=6-13 animals for each group, *P<0.001 vs. BF control, #P<0.05 vs. FFH group, analyzed by one-way ANOVA followed by Fisher's LSD Test). (b) Morphological analysis of rat intestinal samples in experimental NEC at day 4. Panel A represents an ileal segment from a BF animal showing normal histology (the villi are tall and healthy). Panel B represents an ileal segment from a FFH animal showing fewer Goblet cells, villus core separation and presence of inflammatory cells (black arrows). Panel C represents an ileal segment from a FFH animal that received semapimod (0.75 mg/kg, i.p.) and displays a similar morphology as BF control. (c) A representative blot with 3 animals/group and densitometric analysis for RAGE protein (45 and 25 kDa bands) performed as described. Results in graph bars are the mean±S.E.M. (n=9-24 animals for each group, *P=0.001 vs. BF control, #P=0.009 vs. FFH, **P=0.016 vs. BF control, analyzed by one-way ANOVA followed by Tukey Test).

Figure 4A:
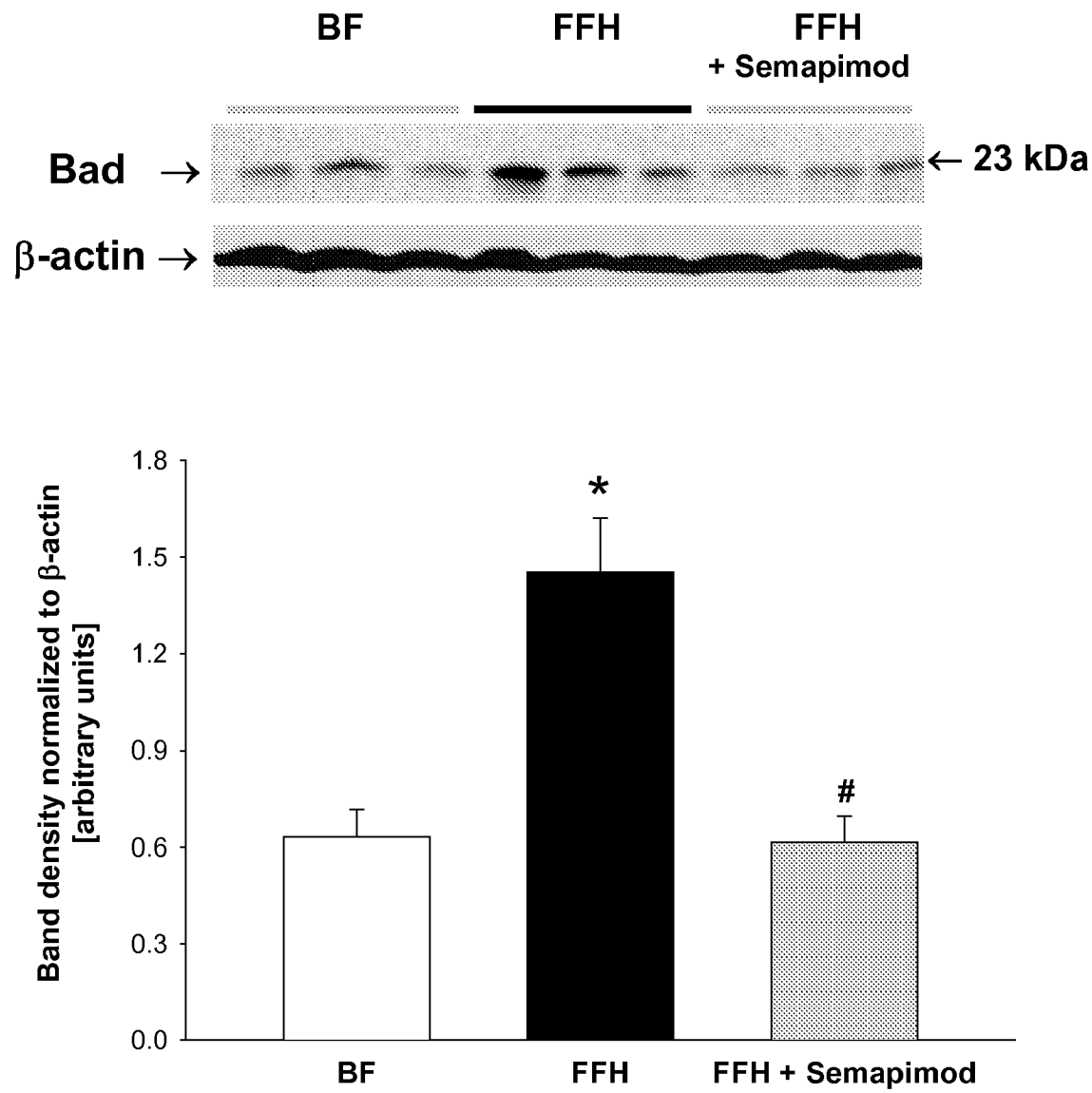
FIG. 4 shows that administration of semapimod in vivo decreases the expression of the Bcl-2 family members Bad and Bax in an experimental NEC model in rats.
Figure 4B:
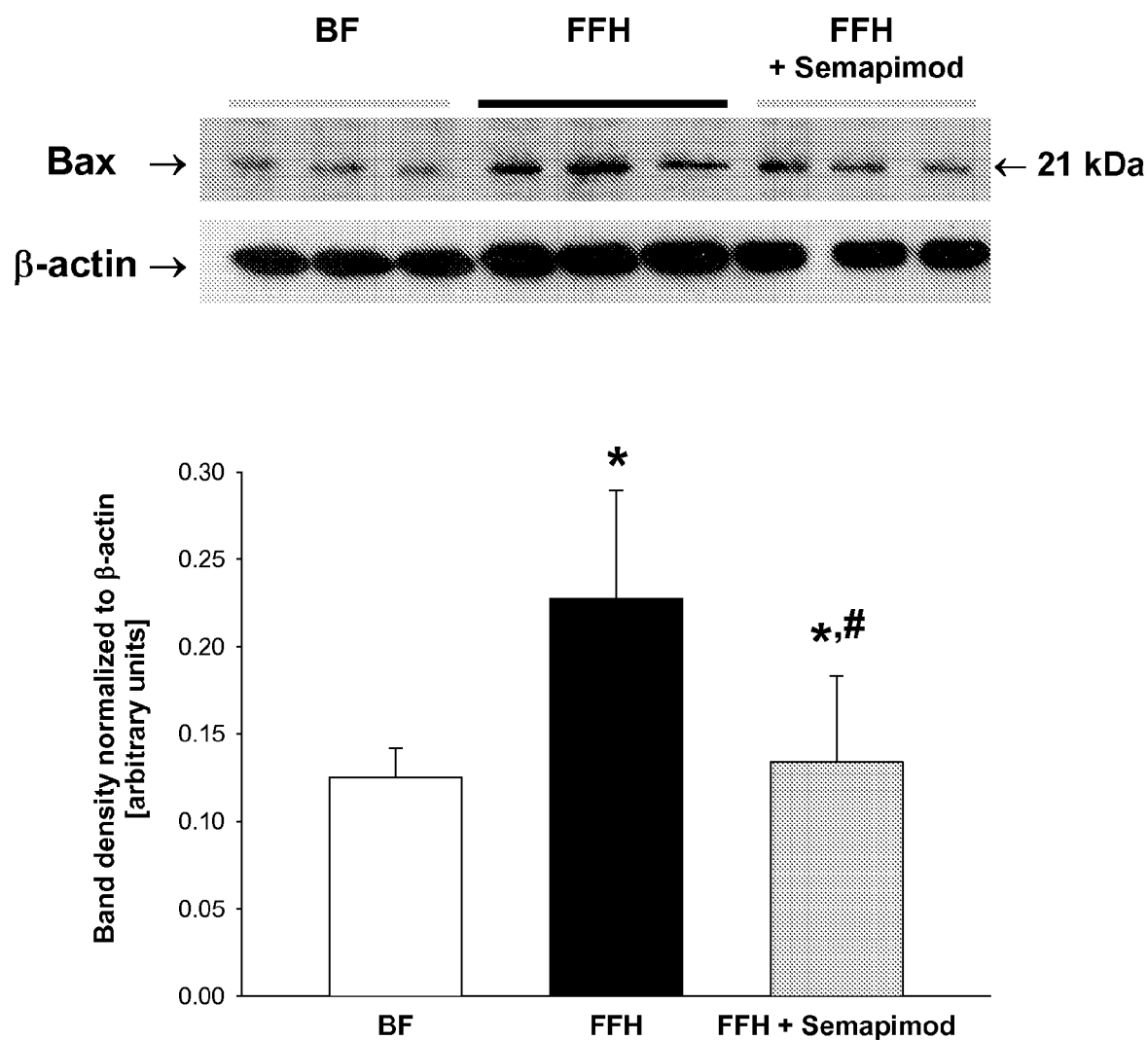

As shown in FIG. 4, the administration of semapimod in vivo decreases the expression of the Bcl-2 family members Bad and Bax in an experimental NEC model in rats. Newborn rats were randomized into three groups: BF represents breast-fed animals left with their mothers (controls), FFH are formula-fed pups exposed to hypoxia, and FFH+semapimod represents animals exposed to hypoxia after administration of the drug semapimod as described in Methods. The terminal ileum of each rat was harvested on day 4 and the mucosal scrapings were processed for protein isolation followed by Western blogging. (a) A representative blot with 3 animals/group and densitometric analysis for Bad protein. Results in graph bars are the mean±S.E.M. (n=17-22 animals for each group, *P<0.001 vs. BF control, #P<0.001 vs. FFH group, analyzed by one-way ANOVA followed by Tukey Test). (b) A representative blot with 3 animals/group and densitometric analysis for Bax protein. Results in graph bars are the mean±S.E.M. (n=4 animals for each group, *P<0.005 vs. BF control, #P<0.005 vs. FFH group, analyzed by one-way ANOVA followed by Fisher's LSD Test).

As shown in FIG. 4, the administration of semapimod in vivo decreases the expression of iNOS and COX-2 in an experimental NEC model in rats. Newborn rats were randomized into three groups: BF represents breast-fed animals left with their mothers (controls), FFH are formula-fed pups exposed to hypoxia, and FFH+semapimod represents animals exposed to hypoxia after administration of the drug semapimod as described in Methods. The terminal ileum of each rat was harvested on day 4 and the mucosal scrapings were processed for protein isolation followed by Western blotting. (a) A representative blot with 3 animals/group and densitometric analysis for iNOS protein. Results in graph bars are the mean±S.E.M. (n=29 animals for each group, *P<0.001 vs. BF control, #P=0.006 vs. FFH group, analyzed by one-way ANOVA followed by Tukey Test). (b) A representative blot with 3 animals/group and densitometric analysis for COX-2 protein. Results in graph bars are the mean±S.E.M. (n=16-27 animals for each group, *P<0.001 vs. BF control, #P=0.05 vs. FFH group, analyzed by one-way ANOVA followed by Tukey Test).

As shown in FIG. 6, semapimod decreases the activation of p38 MAP kinase by LPS in vitro. (a) Rat intestinal epithelial cells (IEC-6) were pretreated with different doses of the drug (0.1-10 μM) for 1 hr. prior to stimulation with 5 μg/ml LPS for 10 min or (b) were pretreated with semapimod (5 μM) for 1 hr. prior to stimulation with 5 μg/ml LPS or ONOO$^-$ (50 μM) for 10 min. The protein lysates were then collected and Western blotting analysis for phospho-p38 and p38 (loading control) was performed as described in Methods. (a) A representative blot for pp38/p38 and densitometric analysis showing the ratio of pp38/p38 band intensity. Ctrl are non-stimulated cells. Results in graph bars are the mean±S.E.M. (n=3 independent experiments, *P<0.05 vs. LPS treated cells without pretreatment with semapimod, analyzed by one-way ANOVA followed by Fisher's LSD Test).

Figure 7:
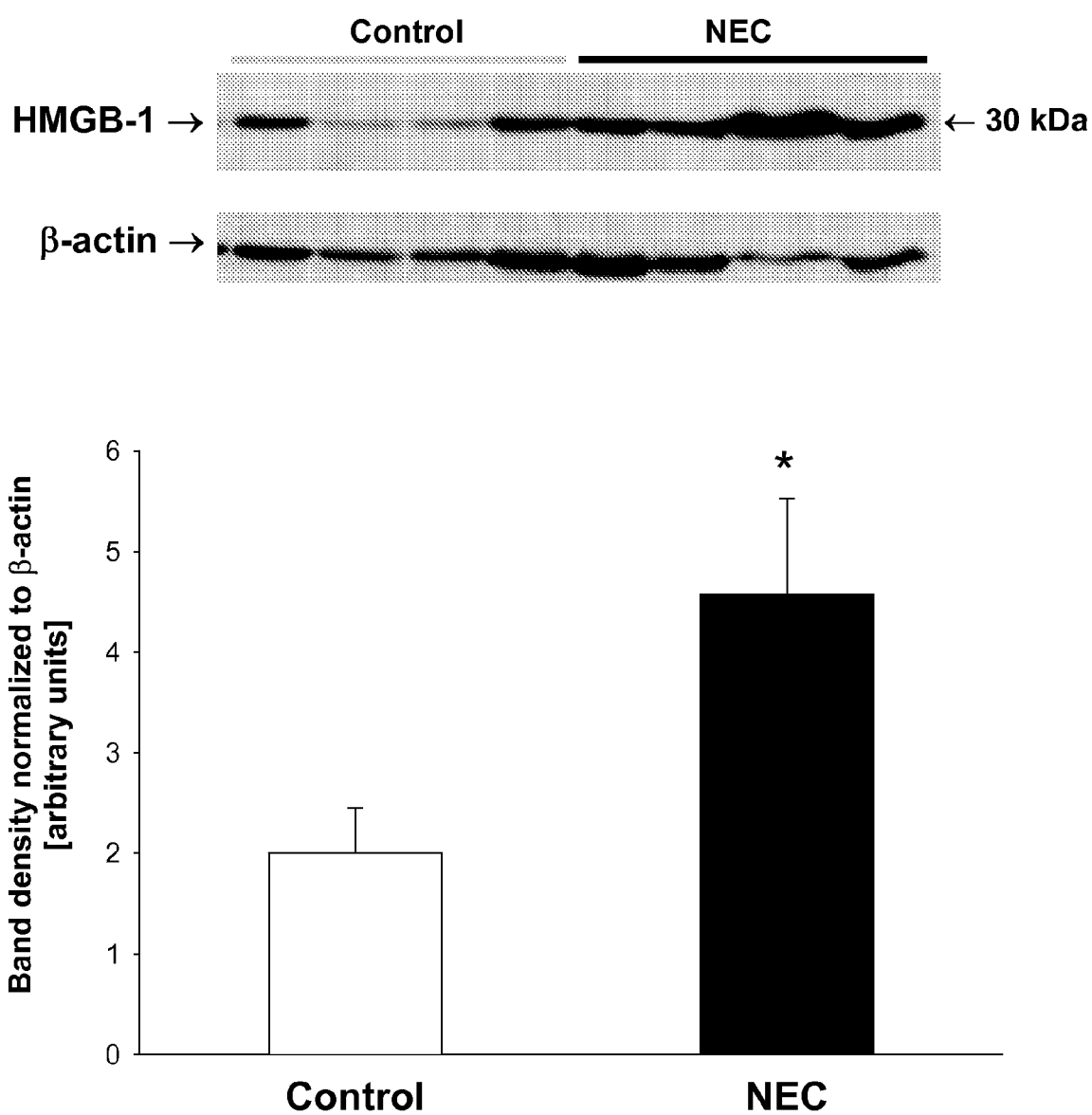
FIG. 7 shows HMGB1 protein expression in human NEC.

As shown in FIG. 7, HMGB1 protein is expressed in human NEC. Representative ileal segments from four neonates undergoing bowel resection for NEC and ileal specimens from four neonates undergoing intestinal resection for inflammatory conditions other than NEC (control) were analyzed for the presence of HMGB1. The frozen intestinal samples were processed and Western blotting was performed as described under Materials and Methods with 50 μg protein per lane. Results in graph bars are the mean±S.D. (n=7 patients/group in two independent experiments, *P<0.05 vs. control, analyzed by Student's t-test).

Overall Mortality in Animal Model of NEC

Newborn rats were fed either breast milk (BF) or a commercial formula (FF) up to four days, with or without a 10-min hypoxic insult thrice as indicated in the Methods section. While breast fed animals gained weight in a normal fashion, formula-fed animals gained significantly less weight than their breast-fed counterparts (32). Moreover, the present inventors observed a higher mortality rate (days 0-3) in the formula-fed animals as compared to the breast-fed group: 34.33% for FFH rats (484/1410) vs. 1.13% for BF controls (8/707) (P<0.001, analyzed by Chi-square test.) The total numbers of animals are cumulative.

Table 1. Time course effect of formula feeding and hypoxia on incidence of NEC.

| | Incidence of NEC (%) | | | |
|---|---|---|---|---|
| | BF | | FFH | |
| day 1 | 6.6 | (91) | 22 | (109) |
| day 2 | 0 | (55) | 33.3 | (84) |
| day 3 | 2.1 | (94) | 40 | (127) |
| day 4 | 2.3 | (390) | 48.3 | (487) |

Newborn rats were randomized into two groups: breast-fed (BF) animals were left with their mothers, and formula-fed pups were exposed to hypoxia (FFH) as described in Methods. The terminal ileum of each rat was harvested on the day indicated, fixed and stained for morphological analysis as described. The data presented in Table 1 is the percentage of rats in each group with incidence of intestinal damage graded between 1 and 3. The numbers in parentheses are the total number of animals/group.

Morphological Changes of Intestinal Samples in Experimental NEC

The present inventors have previously shown that morphologic analysis of ilea from 4 day-old formula-fed rats revealed various degrees of intestinal inflammation compared to ileal segments from breast-fed controls. These inflammatory changes closely resembled the histologic alterations observed in human NEC samples (32). In order to determine the kinetics of the development of intestinal inflammation in this model, both breast-fed and formula-fed animals were sacrificed on each consecutive day after birth and the last 2 cm of their distal ilea were harvested for morphological analysis. The specimens for day 0 were from animals sacrificed within 3 hr after birth and showed minimal morphological changes (18.8% had a histological score of <1, n=48 animals). The overall incidence of morphological and pathological changes characteristic of NEC is shown in Table 1. Intestines of breast-fed pups were normal and rarely showed abnormal morphology. In contrast, in the FFH group morphological evidence of NEC was detected as early as day 1 (mainly villous core separation and presence of occasional neutrophils) with moderate to severe damage at day 4 (histological scores higher than or equal to 1). Analysis of ileal specimens from FFH newborn rats sacrificed at day 5 or day 7 showed severe intestinal damage but not significantly different from FFH animals on day 4 (not shown). Based on this observation, subsequent studies were performed utilizing the intestinal samples harvested from BF animals and FFH animals exposed to hypoxia sacrificed on day 4 after birth.

Expression of High Mobility Group-1 (HMGB1) Protein and its Receptor RAGE in the Intestine.

In order to determine whether the high mobility group-1 (HMGB1) is expressed in the ileum of newborn rats and whether its expression is related to intestinal damage, the expression of this protein in ileal mucosa from both BF and FFH animals sacrificed on different days was analyzed as described in Methods. Although, the mature HMGB1 protein generally migrates as a 30-kDa band on SDS-PAGE (48), it can also appear as a doublet or two very close bands around 30 kDa, where the lower band is usually more intense (K. Tracey, unpublished observations). It was found that intestines of BF pups showed a basal expression of HMGB1, however, larger protein amounts were present in the ileal mucosa of FFH animals at day 4 (FIG. 1). In some cases those animals that showed histologic evidence of moderate to severe intestinal damage also showed increased expression of a lower molecular weight protein (below the 14 kDa molecular weight marker and referred herein as a 7-10 kDa bands) detected with the same anti-HMGB1 polyclonal antibody (FIG. 1).

Semapimod Protects Against Formula-feeding/Hypoxia-mediated Intestinal Injury and Reduces Ileal HMGB1 and RAGE Protein Expression.

Figure 3A:
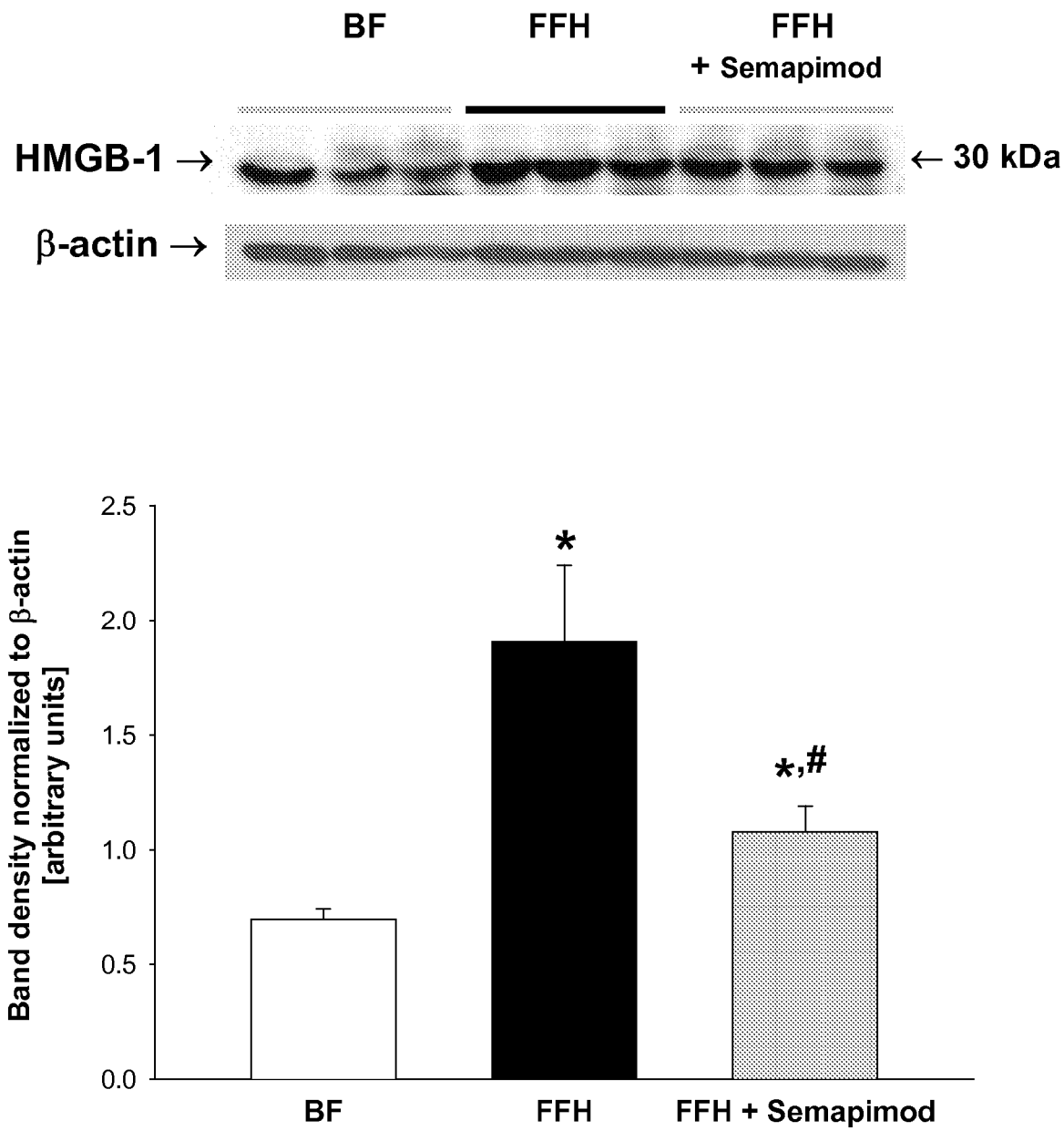
FIG. 3 shows that administration of semapimod in vivo decreases the expression of HMGB1 and its receptor RAGE in ileal samples from formula-fed animals exposed to hypoxia.
Figure 3B:
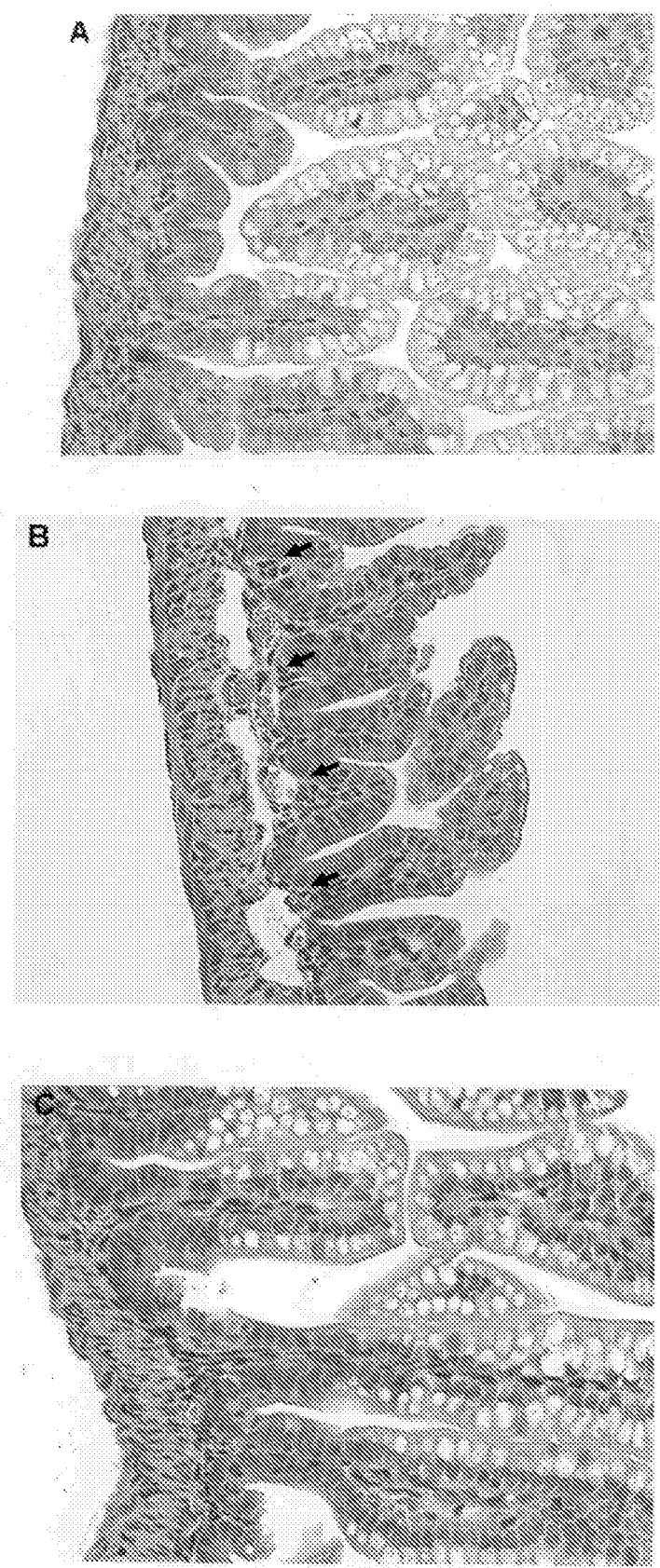
Figure 3C:
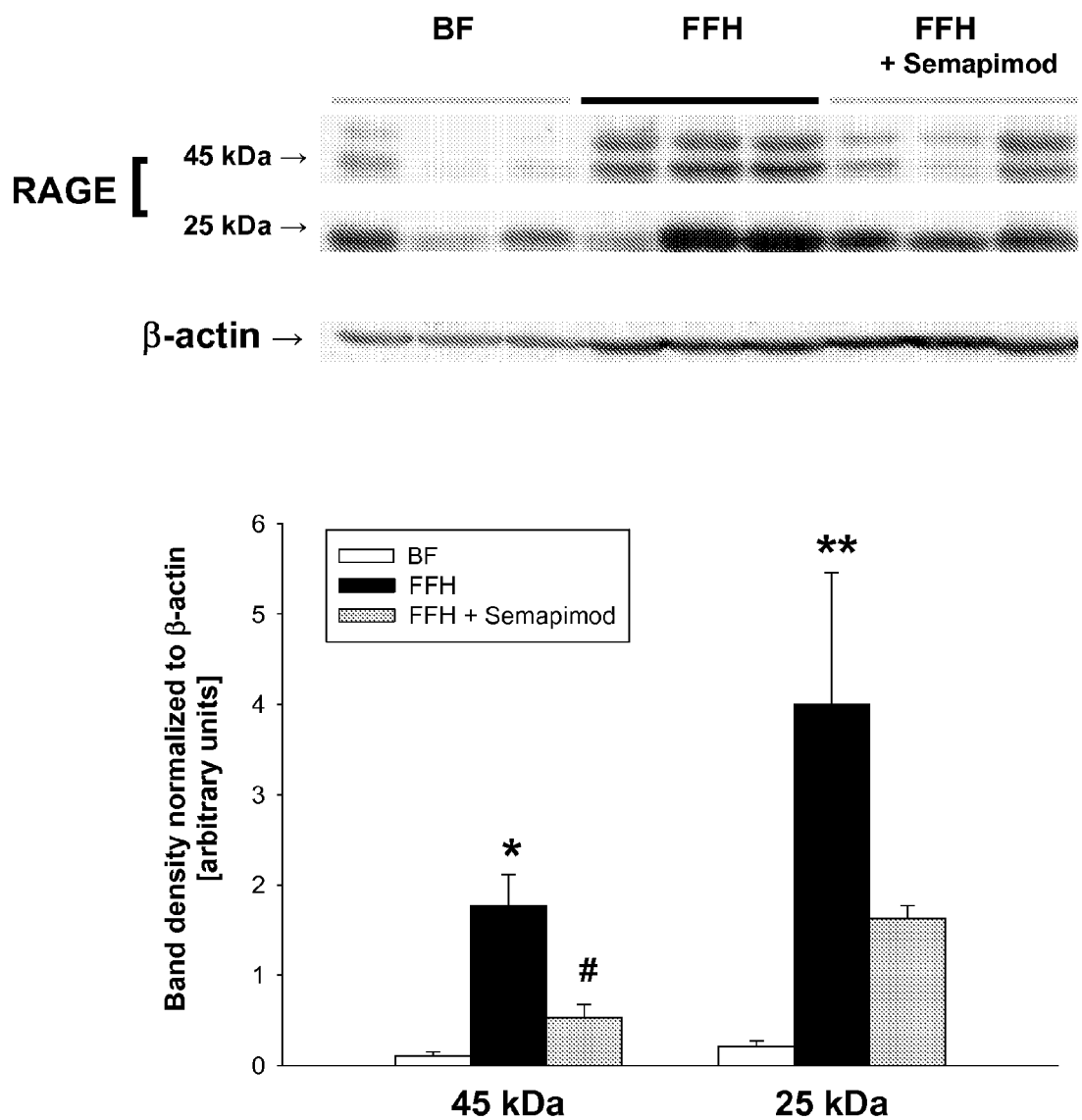

The present inventors hypothesized that the macrophage deactivator semapimod will exert a protective effect against formula-feeding/hypoxia-mediated intestinal injury and that it will affect the expression of the HMGB1 protein. The present inventors found that intraperitoneal administration of semapimod (0.1-1 mg/kg, daily) prevented intestinal damage at doses higher than 0.5 mg/kg, as represented in FIG. 2 as reduction in the incidence of NEC. The present inventors also examined the effect of semapimod on HGMB1 protein expression. While the present inventors found a basal expression of HMGB1 protein in the ileal mucosa of BF animals, a significant increase was observed in the ileal specimens of FFH animals that was reduced after administration of semapimod (FIG. 3a). Administration of vehicle alone had no effect and was not different from FFH group (not shown). This inhibition of protein expression correlated with a decrease in the severity of injury as assessed by histology (FIG. 3b). Receptor signal transduction of HMGB1 occurs in part through the receptor for advanced glycation endproducts (RAGE) in different cell types (2). The present inventors also examined the expression of RAGE in the ileal mucosal scrapings in their NEC model. The anti-RAGE antibody used detects two bands in the 45 kDa range representing the RAGE protein pre and post-glycosylation in mouse lung extract. In addition, this antibody detects a 25 kDa protein believed to be a proteolytic degradation product. The present inventors found that the mucosal scrapings of the FFH rats had a higher expression of RAGE (both the 45 and 25 kDa bands) than the BF controls. Similar to the effect on the HMGB1 in the FFH+Semapimod group, expression of RAGE was reduced after administration of semapimod (FIG. 3c).

Ileal Expression of Inflammatory Proteins in Experimental NEC: Effect of Semapimod The present inventors examined the expression of three members of the Bcl-2 family known to either promote or inhibit apoptosis, namely Bax, Bad and Bcl-2, in the ileal mucosa of newborn rats. The present inventors found that formula feeding and hypoxia significantly upregulate the expression of the apoptotic proteins Bad and Bax in the mucosal scrapings of FFH animals as compared to BF controls (FIG. 4). Expression of both proteins in FFH pups was significantly decreased when the animals were administered the drug semapimod (0.75 mg/kg, IP, daily). There was no significant difference in the expression of Bcl-2 in BF and FFH samples (not shown).

Figure 5A:
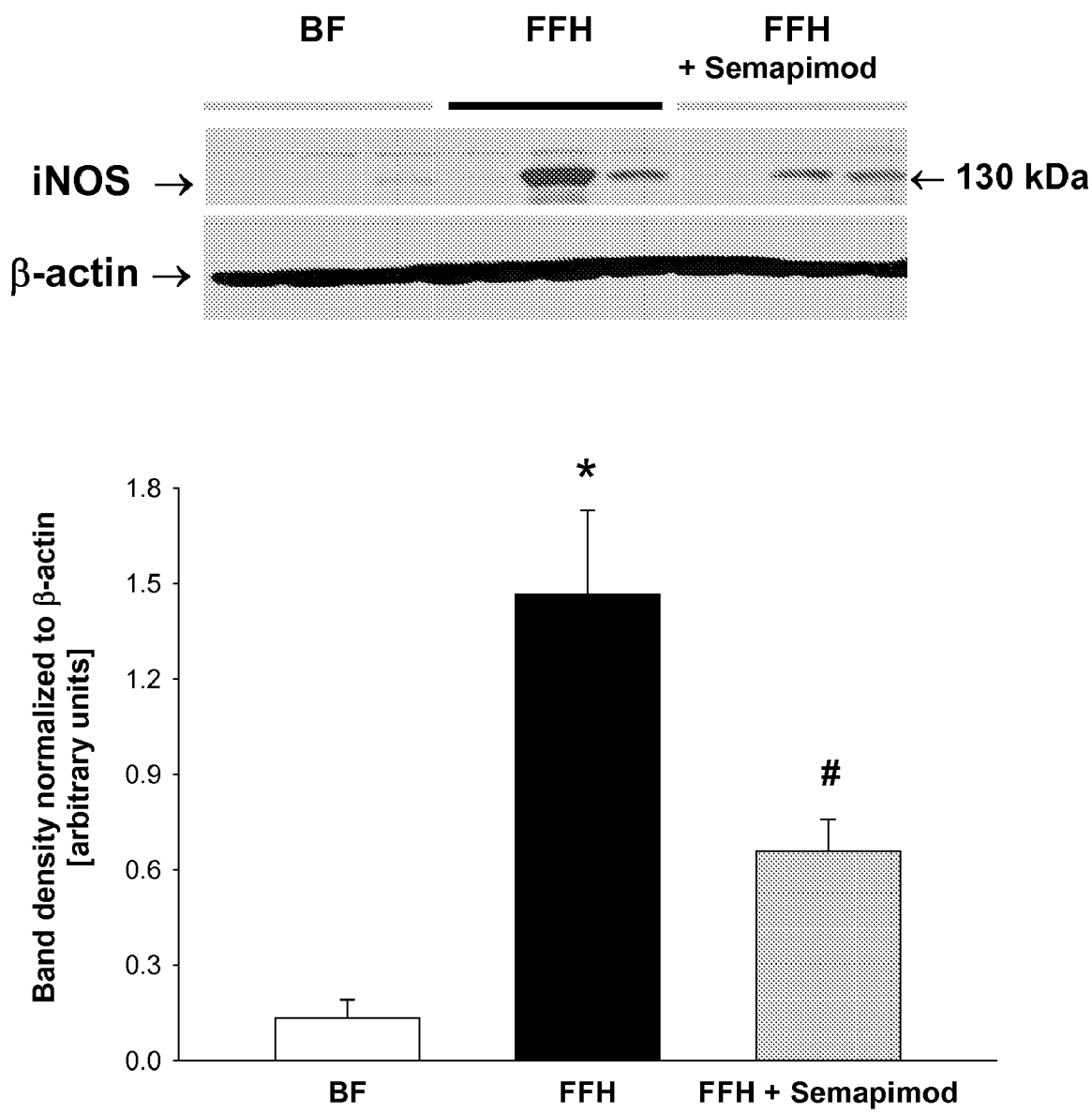
FIG. 5 shows that administration of semapimod in vivo decreases the expression of iNOS and COX-2 in an experimental NEC model in rats.
Figure 5B:
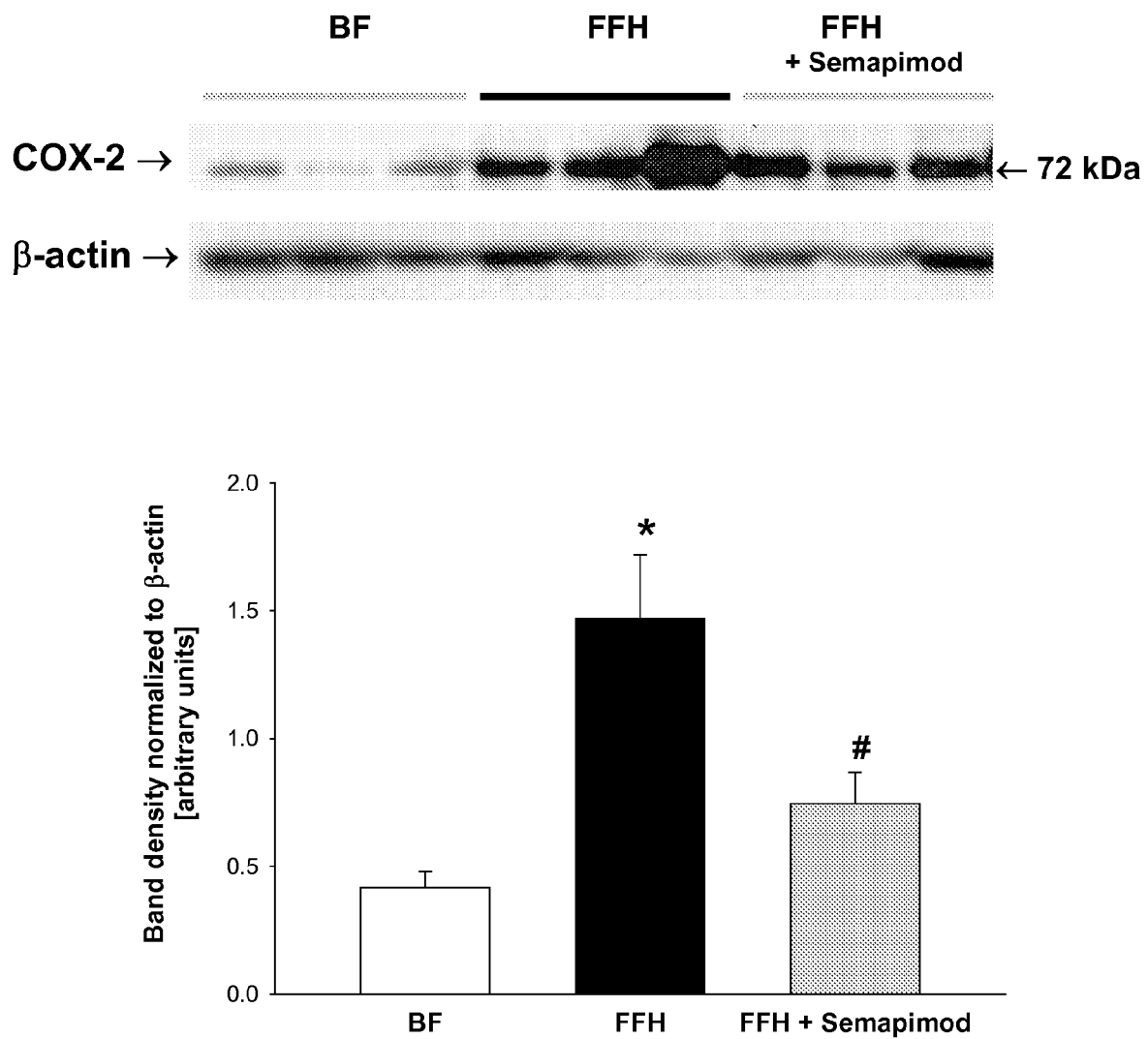

Other proteins whose altered expression has been associated with inflammation in a number of experimental and clinical conditions are iNOS and COX-2. In the NEC model, intestinal samples from BF animals had very little or no iNOS protein as shown by Western blotting (FIG. 5a). Expression of COX-2, however, was present in those samples (FIG. 5b). Elevated levels of iNOS and COX-2 were found in the terminal ileum from FFH newborn rats as compared to BF controls. Expression of both proteins was significantly decreased when FFH animals where administered the drug semapimod (0.75 mg/kg, IP, daily) (FIG. 5).

Figure 6A:
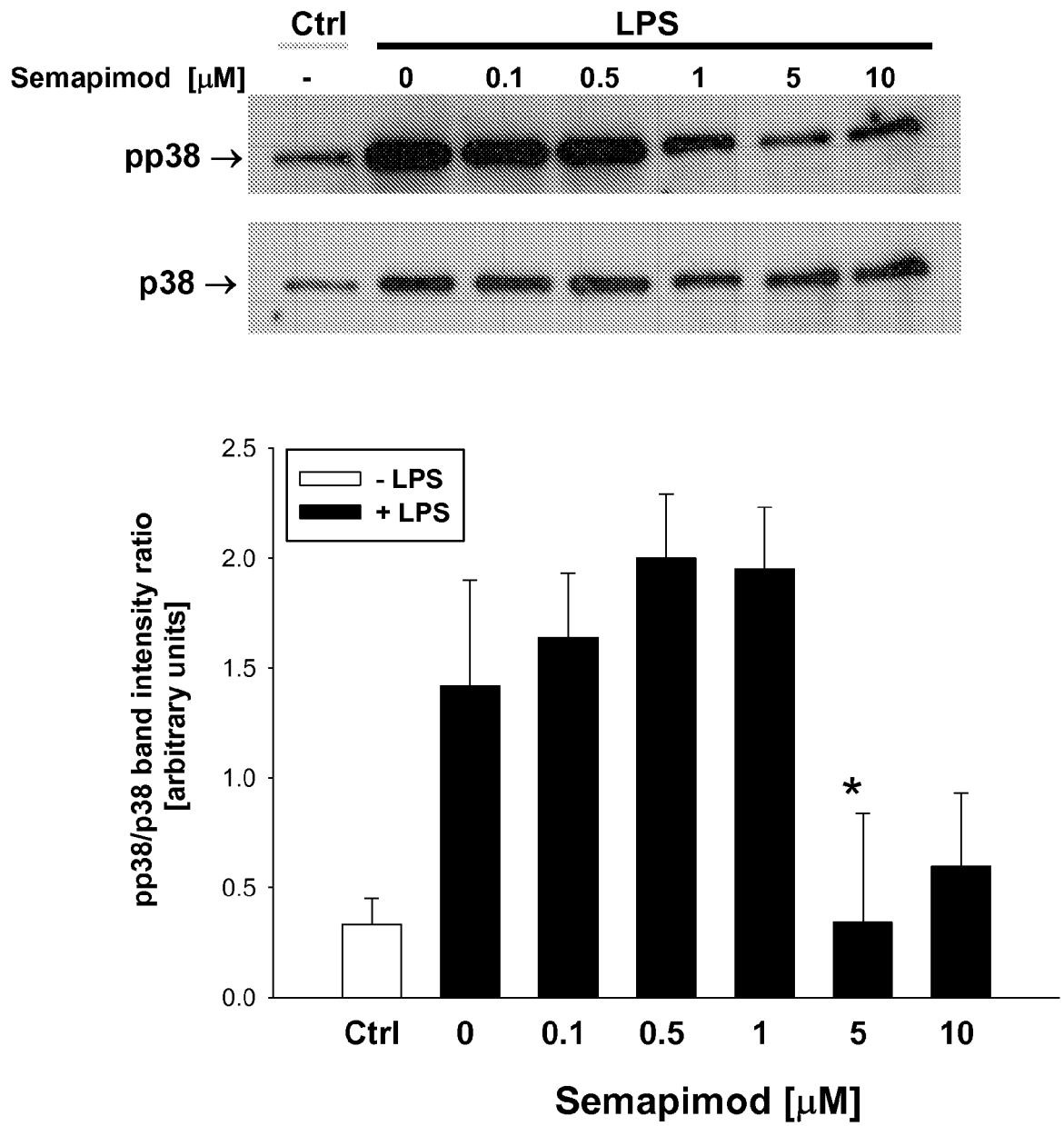
FIG. 6 shows that semapimod decreases the activation of p38 MAP kinase by LPS in vitro.
Figure 6B:
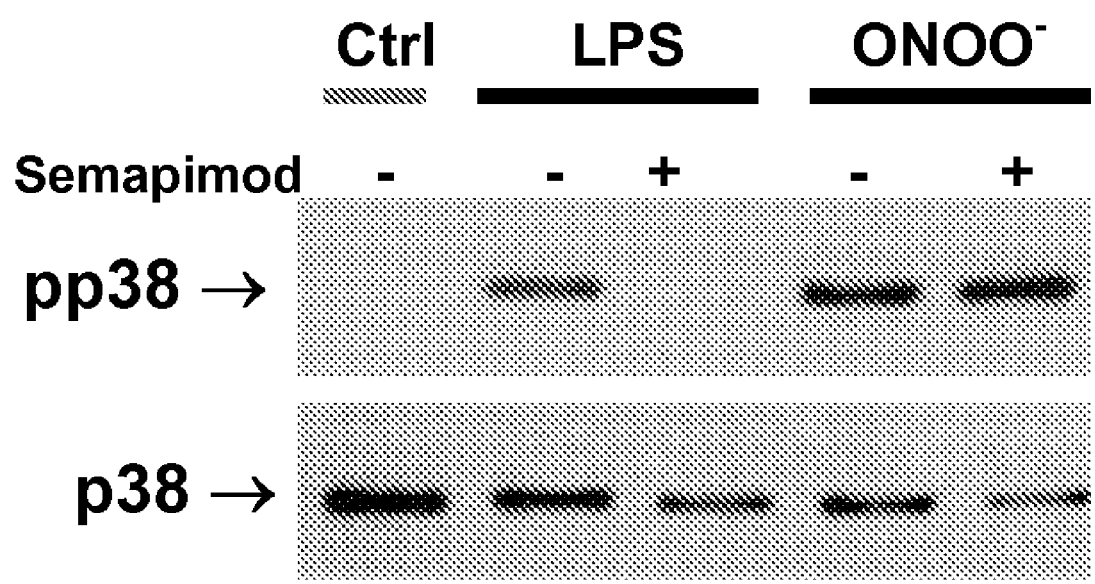

Semapimod Inhibits Activation of p38 Mitogen-activated Protein Kinase (MAP Kinase) by Bacterial LPS in Rat Intestinal Epithelial Cells The present inventors have previously shown that LPS causes rapid but transient activation of p38 MAP kinase as determined by increased phosphorylation of p38. In IEC-6 cells, activating phosphorylation of p38 increases nearly tenfold within 5-10 min of LPS treatment, and returns to basal levels 30 min after addition of LPS (19). In order to examine the effect of semapimod on activation of p38 by LPS, IEC-6 cells were pretreated with different doses of the drug (0.1-10 µM) for 1 hr prior to stimulation with 5 µg/ml LPS for 10 min. The protein lysates were then collected and Western blotting analysis for phospho-p38 and p38 (loading control) was performed as described in Methods. The present inventors found that semapimod dose dependently inhibited the phosphorylation of p38 with a maximal effect at concentrations higher than 1 µM (FIG. 6a). The effect of semapimod on p38 activation by inflammatory mediators other than LPS was evaluated. As shown in FIG. 6b, a similar exposure of IEC-6 cells to ONOO⁻ resulted in a rapid phosphorylation of p38, which in contrast to the LPS-induced effect, was not inhibited by 1 hr pretreatment with 5 µM semapimod. Pretreatment with semapimod also failed to inhibit the stimulatory effect on p38 activation by a mixture of TNFα, IL-1β and IFN-γ (not shown).

HMGB1 is Increased in Human Intestinal Specimens from Patients with Acute NEC

Intestinal specimens from seven infants with acute NEC and control intestinal specimens from seven patients who underwent intestinal resection for inflammatory conditions other than NEC were analyzed by Western blot for the presence of HMGB1 protein in two independent experiments. The frozen samples (segments from whole distal ileum) were processed as described above, and the results are shown in FIG. 7. In contrast to the intestinal specimens from the control patients, ileal specimens from NEC patients demonstrated a two-fold increase in the levels HMGB1 protein. This finding correlates with upregulation of iNOS protein (Zuckerbraun et al., *Am. J. Physiol. Gastrointest. Liver Physiol.*, in press) and higher levels of nitroso species (Zamora et al., *Free Rad. Biol. Med.*, in press) in resected ileal segments from infants with acute NEC.

The relevant portion of each of the following references is hereby incorporated by reference, the same as if set forth at length:

1. Abanese C T and Rothe present inventors MI. Necrotizing enterocolitis. *Semin Pediatr Surg* 4: 200-206, 1995.
2. Andersson U and Tracey K J. HMGB1 in sepsis. *Scand J Infect Dis* 35: 577-584, 2003.
3. Andersson U, Wang H, Palmblad K, Aveberger A C, Bloom O, Erlandsson-Harris H, Janson A, Kokkola R, Zhang M, Yang H and Tracey K J. High mobility group 1 protein (HMG-1) stimulates proinflammatory cytokine synthesis in human monocytes. *J Exp Med* 192: 565-570, 2000.
4. Barlow B and Santulli T V. Importance of multiple episodes of hypoxia or cold stress on the development of enterocolitis in an animal model. *Surgery* 77: 687-690, 1975.
5. Barlow B, Santulli T V, Heird W C, Pitt J, Blanc W A and Schullinger J N. An experimental study of acute neonatal enterocolitis—the importance of breast milk. *J Pediatr Surg* 9: 587-595, 1974.
6. Bernik T R, Friedman S G, Ochani M, DiRaimo R, Ulloa L, Yang H, Sudan S, Czura C J, Ivanova S M and Tracey K J. Pharmacological stimulation of the cholinergic antiinflammatory pathway. *J Exp Med* 195: 781-788, 2002.
7. Bianchi M, Bloom O, Raabe T, Cohen P S, Chesney J, Sherry B, Schmidtmayerova H, Calandra T, Zhang X, Bukrinsky M, Ulrich P, Cerami A and Tracey K J. Suppression of proinflammatory cytokines in monocytes by a tetravalent guanylhydrazone. *J Exp Med* 183: 927-936, 1996.
8. Bucciarelli L G, Wendt T, Rong L, Lalla E, Hofmann M A, Goova M T, Taguchi A, Yan S F, Yan S D, Stern D M and Schmidt A M. RAGE is a multiligand receptor of the immunoglobulin superfamily: implications for homeostatis and chronic disease. *Cell Mol Life Sci* 59: 1117-1128, 2002.
9. Bustin M. Revised nomenclature for high mobility group (HMG) chromosomal proteins. *Trends Biochem Sci* 26: 152-153, 2001.
10. Caplan M S, Lickerman M, Adler L, Dietsch G N and Yu A. The role of recombinant platelet-activating factor acetylhydrolase in a neonatal rat model of necrotizing enterocolitis. *Pediatr Res* 42: 779-783, 1997.
11. Clark J A, Lane R H, Maclennan N K, Holubec H, Dvorakova K, Halpern M D, Williams C S, Payne C M and Dvorak B. Epidermal growth factor reduces intestinal apoptosis in an experimental model of necrotizing enterocolitis. *Am J Physiol Gastrointest Liver Physiol.* 288: G755-G762, 2005.
12. Cohen I T, Nelson S D, Moxley R A, Hirsh M P, Counihan T C and martin R F. Necrotizing enterocolitis in a neonatal piglet model. *J Pediatr Surg* 26: 598-601, 1991.
13. Cohen P S, Nakshatri H, Dennis J, Caragine T, Bianchi M, Cerami A and Tracey K J, CNI-1493 inhibits monocyte/macrophage tumor necrosis factor by suppression of translation efficiency. *Proc Natl Acad Sci USA* 93: 3967-3971, 1996.
14. Crissinger K D, Burney D L, Velasquez O R and Gonzalez E. An animal model of necrotizing enterocolitis induced by infant formula and ischemia in developing piglets. *Gastroenterology* 106: 1215-1222, 1994.
15. Dickinson E C, Gorga J C, Garrett M, Tuncer R, Boyle P, Watkins S C, Alber S M, Parizhskaya M, Trucco M, Rothe present inventors MI and Ford H R. Immunoglobulin A supplementation abrogates bacterial translocation and preserves the architecture of the intestinal epithelium. *Surgery* 124: 284-290, 1998.
16. Ford H R, Sorrells D L and Knisely A S. Inflammatory cytokines, nitric oxide, and necrotizing enterocolitis, *Semin Pediatr Surg* 5: 155-159, 1996.
17. Ford H R, Watkins S, Reblock K and Rothe present inventors M. The role of inflammatory cytokines and nitric oxide in the pathogenesis of necrotizing enterocolitis, *J Pediatr Surg* 32: 275-282, 1997.
18. Go L L, Albanese C T, Watkins S C, Simmons R L and Rothe protein inventors MI. Breast milk protects the neonate from bacterial translocation. *J Pediatr Surg* 29: 1059-1063, 1994.
19. Grishin A, Wang J, Hackam D, Qureshi F, Upperman J, Zamora R and Ford H R. p38 MAP kinase mediates endotoxin-induced expression of cyclooxygenase-2 in enterocytes. *Surgery* 136: 329-335, 2004.
20. Halpern M D, Holubec H, Dominguez J A, Williams C S, Meza Y G, McWilliam D L, Payne C M, McCuskey R S, Besselsen D G and Dvorak B. Up-regulation of IL-18 and IL-12 in the ileum of neonatal rats with necrotizing enterocolitis. *Pediatr Res* 51: 733-739, 2002.
21. Harris M C, Costarino A T, Jr., Sullivan J S, Dulkerian S, McCawley, L, Corcoran L, Butler S and Kilpatrick L, Cytokine elevations in critically ill infants with sepsis and necrotizing enterocolitis. *J Pediatr* 124: 105-111, 1994.
22. Holman R C, Stehr-Green J K and Zelasky M T. Necrotizing enterocolitis mortality in the United States, 1979-85, *Am J Public Health* 79: 987-989, 1989.
23. Hommes D, van den B B, Plasse T, Bartelsman J, Xu C Macpherson B, Tytgat G, Peppelenbosch M and Van Deventer S. Inhibition of stress-activated MAP kinases induces clinical improvement in moderate to severe Crohn's disease. *Gastroenterology* 122: 7-14, 2002.
24. Hori O, Brett J, Slattery T, Cao R, Zhang J, Chen J X, Nagashim M, Lundh E R, Vijay S, Nitecki D and. The receptor for advanced glycation end products (RAGE) is a cellular binding site for amphoterin. Mediation of neurite outgrowth and co-expression of rage and amphoterin in the developing nervous system. *J Biol Chem* 270: 25752-25761, 1995.
25. Jilling, T, Lu J, Jackson M and Caplan M S. Intestinal epithelial apoptosis initiates gross bowel necrosis in an experimental rat model of neonatal necrotizing enterocolitis. *Pediatr Res* 55: 622-629, 2004.
26. Kliegman R M. Models of the pathogenesis of necrotizing enterocolitis. *J Pediatr* 117: S2-S5, 1990.
27. Kliegman R M and Fanaroff A A. Necrotizing enterocolitis. *N Engl J Med* 310: 1093-1103, 1984.
28. Kubes P and McCafferty D M. Nitric oxide and intestinal inflammation. *Am J Med* 109: 150-158, 2000.
29. Liliensiek B, Weigand M A, Bierhaus A, Niclas W, Kasper M. Hofer S, Plachky J, Grone H J, Kurschus F C, Schmidt A M, Yan S D, Martin E, Schleicher E, Stern D M, Hammerling G G, Nawroth P P and Arnold B. Receptor for advanced glycation end products (RAGE) regulates sepsis but not the adaptive immune response. *J Clin Invest* 113: 1641-1650, 2004.
30. Milligan E D, O'Connor K A, Armstrong C B, Hansen M K, Martin D, Tracey K J, Maier S F and Watkins L R. Systemic administration of CNI-1943, a p38 mitrogen-activated protein kinase inhibitor, blocks intrathecal human immunodeficiency virus-1 gp120-induced enhanced pain states in rats. *J Pain* 2: 326-333, 2001.
31. Molina P E, Qian L, Schuhlein D, Naukam R, Wang H, Tracey K J and Abumrad NN. CNI-1493 attenuates hemodynamic and pro-inflammatory responses to LPS. *Shock* 10: 329-334, 1998.
32. Nadler E P, Dickinson E, Knisely A, Zhang X R, Boyle P, Beer-Stolz D, Watkins S C and Ford H R. Expression of inducible nitric oxide synthase and interleukin-12 in experimental necrotizing enterocolitis. *J Surg Res* 92: 71-77, 2000.
33. Nadler E P, Stanford A, Zhang, X R, Schall L C, Alber S M, Watkins S C and Ford H R. Intestinal cytokine gene expression in infants with acute necrotizing enterocolitis: interleukin-11 mRNA expression inversely correlates with extent of disease. *J Pediatr Surg* 36: 1122-1129, 2001.
34. Ochoa J B, Udekwu A O, Billiar T R, Curran R D, Cerra F B, Simmons R I, and Peitzman A B. Nitrogen oxide levels in patients after trauma and during sepsis. *Ann Surg* 214: 621-626, 1991.
35. Park J S, Svetkauskaite D, He Q, Kim J Y, Strassheim D, Ishizaka A and Abraham E. Involvement of toll-like receptors 2 and 4 in cellular activation by high mobility group box 1 protein. *J Biol Chem* 279: 7370-7377, 2004.
36. Potoka D A, Upperman J S, Zhang X R, Kaplan J R, Corey S J, Grishin A, Zamora R and Ford H R. Peroxynitrite inhibits enterocyte proliferation and modulates Src kinase activity in vitro. *Am J Physiol Gastrointest Liver Physiol* 285: G861-G869, 2003.
37. Rothe present inventors MI, Reblock KK, Kurkehubasche A G and Healey P J. Necrotizing enterocolitis in the extremely low birth weight infant. *J Pediatr Surg* 29: 987-990, 1994.
38. Sappington P L, Yang R, Yang H, Tracey K J, Delude R L and Fink M P. HMGB1 B box increases the permeability of Caco-2 enterocytic monolayers and impairs intestinal barrier function in mice. *Gastroenterology* 123: 790-802, 2002.
39. Scaffidi P, Misteli T and Bianchi M E. Release of chromatin protein HMGB1 by necrotic cells triggers inflammation. *Nature* 418: 191-195, 2002.
40. Scheifele D W. Role of bacterial toxins in neonatal necrotizing enterocolitis. *J Pediatr* 117: S44-S46, 1990.
41. Shi Y, Li H Q, Shen C K, Wang J H, Qin S W, Liu R and Pan J. Plasma nitric oxide levels in newborn infants with sepsis. *J Pediatr* 123: 435-438, 1993.
42. Sitaraman S V, Hoteit M and Gewirtz A T. Semapimod. Cytokine. *Curr Opin Investig Drugs* 4: 1363-1368, 2003.
43. Sorrells D L, Friend C, Koltuksuz U, Courcoulas, A, Boyle P, Garrett M, Watkins S, Rothe present inventors MI and Ford H R. Inhibition of nitric oxide with aminoguanidine reduce bacterial translocation after endotoxin challenge in vivo. *Arch Surg* 131: 1155-1163, 1996.
44. Wang H, Bloom O, Zhang, M, Vishnubhakat J M, Ombrellino M. Che J, Frazier A, Yang H, Ivanova S, Borovikova L, Manogue K R, Faist E, Abraham E, Andersson J, Andersson U, Molina P E, Abumrad N N, Sama A and Tracey K J. HMG-1 as a late mediator of endotoxin lethality in mice. *Science* 285: 284-251, 1999.
45. Wang H, Yang H and Tracey K J. Extracellular role of HMGB1 in inflammation and sepsis. *J Intern Med* 255: 320-331, 2004.
46. Warner T D and Mitchell J A. Cyclooxygenases: new forms, new inhibitors, and lessons from the clinic. *FASEB J* 18: 790-804, 2004.
47. Wilson R, Kanto W P, Jr., McCarthy B J and Feldman R A. Age at onset of necrotizing enterocolitis. Risk factors in small infants. *Am J Dis Child* 136: 814-816, 1982.
48. Yang H, Wang H and Tracey K J. HMG-1 rediscovered as a cytokine. *Shock* 15: 247-253, 2001.
49. Zamora R, Vodovotz Y, Aulak K S, Kim P K, Kane J M, III, Alarcon L, Stuehr D J and Billiar T R. A DNA microarray study of nitric oxide-induced genes in mouse heptaocytes: implications for hepatic heme oxygenase-1 expression in ischemia/reperfusion. *Nitric Oxide* 7: 165-186, 2002.
50. Zamora R, Vodovotz Y and Billiar T R. Inducible nitric oxide synthase and inflammatory diseases. *Mol Med* 6: 347-373, 2000.
51. Zill H, Gunther R, Erbersdobler H F, Folsch U R and Faist V. RAGE expression and AGE-induced MAP kinase activation in Caco-2 cells. *Biochem Biophys Res Commun* 288: 1108-111, 2001.

From the description herein, it will be clear to those skilled in the art that changes and modifications can be made to the embodiments described herein without departing from the invention. It should be understood, therefore, that the invention is not limited to only the disclosed embodiments.

The invention claimed is:

1. A method, comprising administering to a subject in need thereof, a compound having the following formula:

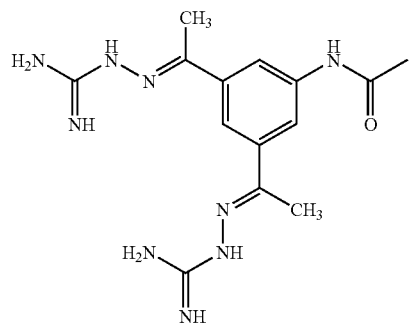

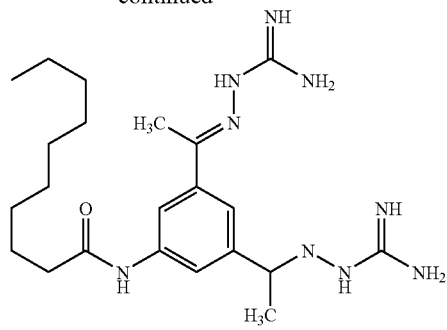

a salt thereof, or a combination of the compound and a salt thereof, for the treatment of necrotizing enterocolitis (NEC).

2. The method of claim 1, wherein the subject is a human subject.

3. The method of claim 1, wherein the subject is a human infant.

4. The method of claim 1, wherein the compound is in the salt form.

5. The method of claim 1, wherein the compound, salt thereof, or a combination of the compound and a salt thereof, is administered in the form of a composition further comprising at least one carrier.

6. The method of claim 1, wherein the salt is a salt of L-lactic acid.

7. The method of claim 1, wherein the salt is a bromide, iodide, nitrate, sulfate, bisulfate, phosphate, acid phosphate, citrate, acid citrate, tartrate, bitartrate, succinate, fumarate, tosylate, mesylate, gluconate, saccharate, benzoate, methanesulfonate, ethanesulfonate, benzenesulfonate, or pamoate salt of said compound.

8. The method of claim 1, wherein the salt is a bicarbonate, edetate, camsylate, carbonate, dihydrochloride, edisylate, estolate, gluceptate, glucoheptonate, glutamate, hydrobromide, hydrochloride, hydroxynaphthoate, chloride, isethionate, lactate, malate, mandelate, methyibromide, methylnitrate, methylsulfate, mucate, napsylate, pantothenate, diphosphate, salicylate, stearate, subacetate, tannate, teoclate, or triethiodide salt of said compound.

9. The method of claim 1, wherein the salt is an acid addition salt of hydrochloric, phosphoric, acetic, oxalic, tartaric, or mandelic acid.

* * * * *